(12) United States Patent
Schwarz et al.

(10) Patent No.: US 9,919,161 B2
(45) Date of Patent: *Mar. 20, 2018

(54) METHOD OF NEURAL STRUCTURE STIMULATION BY MAGNETIC FIELD

(71) Applicant: BTL HOLDINGS LIMITED, Nicosia (CY)

(72) Inventors: Tomáš Schwarz, Prague (CZ); Ondra Prouza, Říčany u Prahy (CZ)

(73) Assignee: BTL Holdings Limited, Nicosia (CY)

( * ) Notice: Subject to any disclaimer, the term of this patent is extended or adjusted under 35 U.S.C. 154(b) by 0 days.

This patent is subject to a terminal disclaimer.

(21) Appl. No.: 15/073,318

(22) Filed: Mar. 17, 2016

(65) Prior Publication Data

US 2017/0001026 A1 Jan. 5, 2017

Related U.S. Application Data

(63) Continuation-in-part of application No. 14/951,093, filed on Nov. 24, 2015, and a continuation-in-part of application No. 14/926,365, filed on Oct. 29, 2015, and a continuation-in-part of application No. 14/789,658, filed on Jul. 1, 2015, and a continuation-in-part of application No. 14/873,110, filed on Oct. 1, 2015, which is a continuation of (Continued)

(51) Int. Cl.
*A61N 2/00* (2006.01)
*A61N 2/02* (2006.01)

(52) U.S. Cl.
CPC ............. *A61N 2/006* (2013.01); *A61N 2/008* (2013.01); *A61N 2/02* (2013.01)

(58) Field of Classification Search
CPC .... A61N 2/006; A61N 2/02; A63B 21/00181; A63B 71/0009; A63B 71/0076; A63B 71/0664; A63B 71/0605; A63B 22/0076; A63B 22/0664; A63B 22/0605; A63B 2220/54; A63B 2213/004
USPC ........................................................ 600/9–15
See application file for complete search history.

(56) References Cited

U.S. PATENT DOCUMENTS 4,665,898 A * 5/1987 Costa ........................ A61N 2/02
600/14
4,993,413 A * 2/1991 McLeod .................. A61N 2/02
600/13

(Continued)

FOREIGN PATENT DOCUMENTS

EP 0209246 A1 1/1987
EP 2676700 A2 12/2013

(Continued)

OTHER PUBLICATIONS

European Commission, Neuodegenerative Disorders, 10 pages printed Dec. 27, 2016.*

(Continued)

*Primary Examiner* — Samuel Gilbert
(74) *Attorney, Agent, or Firm* — Kenneth H. Ohriner; Perkins Coie LLP

(57) ABSTRACT

The present invention relates to apparatus and methods for stimulation and/or treatment of neural structure by high power time-varying magnetic field. The stimulation is followed by at least modulation of action potential of neural structure. The apparatus and methods may be used e.g. in physiotherapy, psychotherapy, psychiatry or addiction treatment.

30 Claims, 12 Drawing Sheets

Related U.S. Application Data application No. 14/789,156, filed on Jul. 1, 2015, now abandoned.

(56) References Cited

U.S. PATENT DOCUMENTS

| | | | |
|---|---|---|---|
| 5,085,626 A | 2/1992 | Frey | |
| 5,401,233 A | 3/1995 | Erickson et al. | |
| 5,984,854 A | 11/1999 | Ishikawa et al. | |
| 6,117,066 A | 9/2000 | Abrams | |
| 6,179,769 B1 | 1/2001 | Ishikawa et al. | |
| 6,213,933 B1* | 4/2001 | Lin | A61N 2/02 600/13 |
| 6,402,678 B1* | 6/2002 | Fischell | A61N 2/02 600/13 |
| 6,527,694 B1 | 3/2003 | Ishikawa et al. | |
| 7,601,115 B2 | 10/2009 | Riehl | |
| 7,740,574 B2* | 6/2010 | Pilla | A61H 39/002 600/13 |
| 7,744,523 B2 | 6/2010 | Epstein | |
| 7,946,973 B2 | 5/2011 | Peterchev | |
| 9,002,477 B2 | 4/2015 | Burnett | |
| 2001/0031906 A1 | 10/2001 | Ishikawa et al. | |
| 2006/0152301 A1* | 7/2006 | Rohwedder | B06B 1/0215 333/105 |
| 2006/0187607 A1 | 8/2006 | Mo | |
| 2008/0262287 A1 | 10/2008 | Dussau | |
| 2010/0087699 A1 | 4/2010 | Peterchev | |
| 2010/0331603 A1* | 12/2010 | Szecsi | A61N 2/006 600/13 |
| 2011/0021863 A1 | 1/2011 | Burnett | |
| 2012/0053449 A1 | 3/2012 | Moses | |
| 2013/0238061 A1 | 9/2013 | Edoute | |
| 2013/0317281 A1 | 11/2013 | Schneider | |
| 2014/0046423 A1 | 2/2014 | Rajguru | |
| 2015/0025299 A1 | 1/2015 | Edoute | |
| 2015/0157873 A1 | 6/2015 | Sokolowski | |
| 2015/0367141 A1* | 12/2015 | Goetz | A61N 2/02 600/14 |
| 2016/0030763 A1* | 2/2016 | Midorikawa | A61N 2/004 600/13 |

FOREIGN PATENT DOCUMENTS

| | | |
|---|---|---|
| WO | 2002/025675 A1 | 3/2002 |
| WO | 2003/090863 A1 | 11/2003 |
| WO | 2004087255 A1 | 10/2004 |
| WO | 2008109058 A1 | 9/2008 |
| WO | 2010135425 A1 | 11/2010 |
| WO | 2015012672 A1 | 1/2015 |

OTHER PUBLICATIONS

Polk, Charles, "Therapeutic Applications of Low-Frequency Sinusoidal and Pulsed Electric and Magnetic Fields," The Biomedical Engineering Handbook, vol. I, 2000, Second edition, pp. 1625-1636.

Heisel, Jürgen, Physikalische Medizin. Stuttgart: Georg Thieme Verlag KG, 2005. ISBN 3-13-139881-7. p. 159.

World Health Organization, "The Atlas: Epilepsy Care in the World", pp. 1-96 (2005).

Robert S. Fisher et al., "A practical clinical definition of epilepsy", Epilepsia, 55(4): pp. 475-482 (2014).

National Institute of Neurological Disorders and Stroke, Epilepsy Information Page, www.ninds.nih.gov/disorders/epilepsy/epilepsy.htm, pp. 1-6 (Feb. 1, 2016).

Christine Lineham et al., Brainwave the Irish Epilepsy Assoication, "The Prevalence of Epilepsy in Ireland" Summary Report, pp. 1-8 (May 2009).

World Health Organization, "Neurological Disorders—Public Health Challenges", pp. 1-232 (2006).

European Patent Office, International Search Report and Written Opinion for International Application No. PCT/IB2016/053930; dated Dec. 12, 2016; 19 pages.

* cited by examiner

METHOD OF NEURAL STRUCTURE STIMULATION BY MAGNETIC FIELD

PRIORITY CLAIM

This application is a Continuation-in-Part of each of the following U.S. patent application Ser. No. 14/951,093 filed Nov. 24, 2015 and now pending; Ser. No. 14/926,365 filed Oct. 29, 2015 and now pending; and Ser. No. 14/789,658 filed Jul. 1, 2015 and now pending. This application is also a Continuation-in-Part of U.S. patent application Ser. No. 14/873,110 filed Oct. 1, 2015 and now pending, which is a Continuation of U.S. patent application Ser. No. 14/789,156 filed Jul. 1, 2015 and now abandoned. Each of these applications is incorporated herein by reference.

FIELD OF THE INVENTION

The present invention generally relates to apparatus and methods using the influence of magnetic and induced electric field on neural structure. The magnetic field is time-varying and high powered producing magnetic flux density sufficient to induce biological response to the magnetic stimulation.

BACKGROUND OF THE INVENTION

Presently, neural structure stimulation for diagnosis or prognosis or causing improvement of patient's well-being is performed by magnet therapy methods using low repetition rate or direct current methods. However, direct current methods require contact with the patient and may be even invasive. These methods can result in skin irritation, painful application especially for high intensity stimulus, discomfort during the treatment, lack of deep tissue stimulation by non-invasive methods, and a lack of patient compliance with a prescribed therapy due to these factors.

Existing methods of magnet therapy generally tend to be limited by the key parameters of repetition rate and/or magnetic flux density. These methods may use high values of magnetic flux density at low repetition rate or vice versa. At repetition rates exceeding 100 Hz existing methods and devices generally do not provide magnetic flux density sufficient to provide effective magnet treatment. Therefore the deeper neural structures stimulation is limited. Generally, stimulation of neural structures exceeding 100 Hz is performed by devices requiring physical contact with a patient, such as electrotherapy devices. Additionally, currently used devices and methods of magnet therapy are unable to reach or exceed the repetition rate resolution of the biological structure, therefore the biological structure is stimulated by discrete pulses of the same shape.

Existing methods are also not able to provide non-invasive stimulation of neural structures by time-varying magnetic field at repetition rates exceeding the frequency resolution of the neural structure. Some systems also require physical contact with the patient since the magnetic field is weak or the stimulation cannot be transferred without the electrical contact. Generally, these known methods are limited to repetition rates reaching 120 Hz in order to provide neural structure stimulation.

SUMMARY OF THE INVENTION

The present invention provides an alternative treatment of neural diseases, diagnoses or prognosis, alleviating pain, myorelaxation, muscle stimulation, tissue healing, sleep improvement or edema reduction. Additionally, the present methods may be provided in combination with traditional medicament treatment.

According to the first application of the invention, the time-varying magnetic field at a magnetic flux density of at least 0.1 T and/or repetition rate at least 100 Hz may be used for stimulation of biological structure for diagnosis, prognosis or improving the patient's well-being.

In another application of the invention, the time-varying magnetic field at higher repetition rate exceeding the repetition rate resolution of the neural structure may be used for generating an envelope of lower repetition frequency than the repetition rate. The envelope may be generated by time-varying magnetic flux density and/or repetition rate and/or impulse duration.

In still another application of the invention, the time-varying magnetic field may be used for stimulation of biological structure to improve the patient's mental health or for influencing the hormonal production and/or balance.

In still another application of the invention, the time-varying magnetic field may also be used for stimulation of deep neural structures e.g., to treat psychiatric and/or neurodegenerative and/or psychiatric diseases, such as treatment of Parkinson's or Alzheimer's disease.

In still another application of the invention, the time-varying magnetic field may be used for stimulation of neural structure to determine whether the neural pathway is impaired or not, or the level of the impairment may be determined. The one approach is stimulating central neural system or peripheral neural structure and determining the feedback, e.g. muscle contraction. The conduction deficiency may be determined via maximal voluntary contraction.

In still another application of the invention, the time-varying magnetic field may also be used for stimulation of neural structure to alleviate pain via central neural system stimulation or via peripheral neural structure. In general, the peripheral neural structure may be stimulated by repetition rates exceeding 100 Hz and/or by envelopes of lower repetition frequencies. The repetition rate and magnetic flux density selectively stimulates different neural structures. The pain is alleviated at specific repetition rates, pulse shapes and/or current densities. The pain alleviation effect may be caused by high power time-varying magnetic field at different levels of neural system. Nevertheless, the method is not limited to the applications to the limbs and the method is able to be applied to stimulation of any muscle.

In still another application of the invention, the time-varying magnetic field may be used for stimulation of neural structure to cause myorelaxation effects. The myorelaxation effects may occur generally during stimulation by time-varying magnetic field of repetition rate at least 100 Hz. However, the neural structure may be stimulated by envelopes at lower repetition frequencies below 100 Hz.

In still another application of the invention, the time-varying magnetic field may be used for stimulation of neural structure to cause muscle stimulation. The muscle stimulation may occur during stimulation by envelopes of repetition frequencies below 100 Hz. The application may be used for stimulation of denervated muscle treatment.

In still another application of the invention, the time-varying magnetic field may be used for stimulation of neural structure to cause healing tissue effect, improve the sleeping patterns or reduce the edema.

Advantages of the present magnet therapy may include: stimulation of the deep neural structures which are problematically stimulated by superficial stimulation; non-invasive and/or non-contact application of magnetic flux density; treatment without removing clothing; absolute non-invasiveness of the stimulation and elimination of skin irritation in the place of time-varying magnetic field application; high rate of acceptability of the stimulation by patients; elimination of stimulation side effects; elimination of the necessity of applicator made of biocompatible materials; providing a clean and sterile applicator; and capability to provide local or area treatment.

Figure 1:
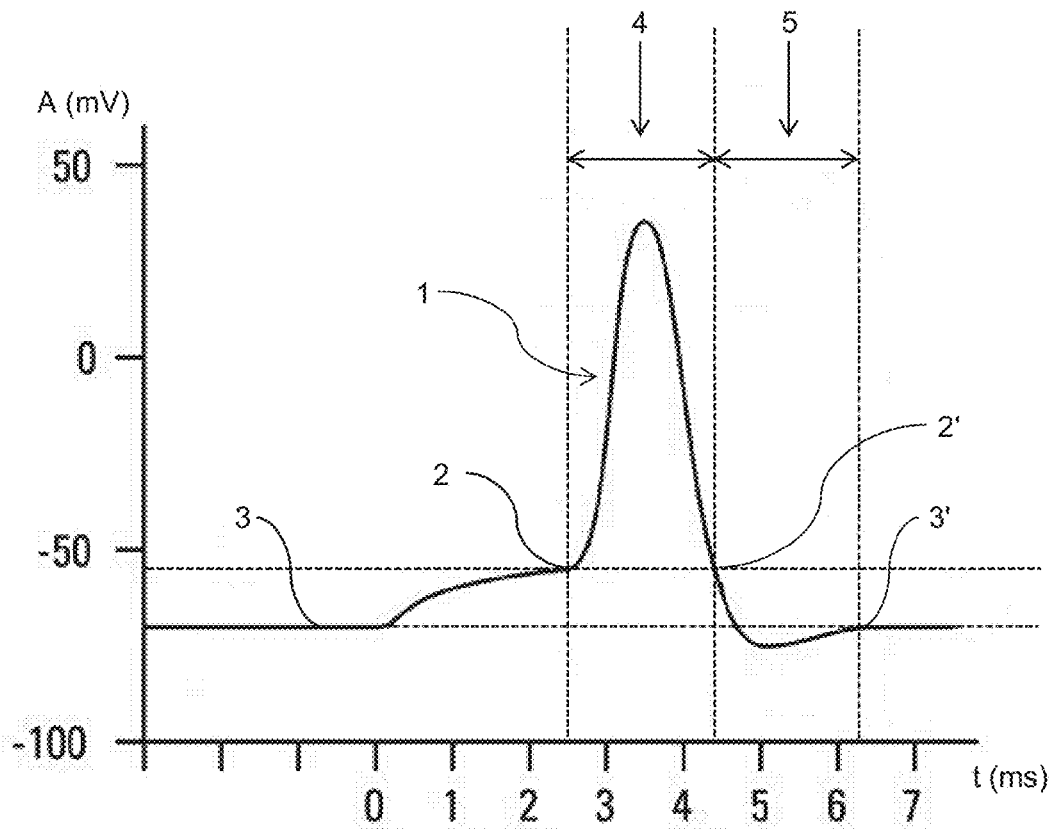
FIG. 1 illustrates an action potential curve of a biological structure.

LIST OF REFERENCE NUMBER 1 curve of action potential
2 threshold potential
2' threshold potential after depolarization
3 resting potential
3' resting potential after action potential
4 absolute refractory period
5 relative refractory period
6 sensory-threshold stimulus
7 below-sensory-threshold stimulus
8 over-sensory-threshold stimulus
9 motor-threshold stimulus
10 below-motor-threshold stimulus
11 over-motor-threshold stimulus
12 noxious-threshold stimulus
13 below-noxious-threshold stimulus
14 over-noxious-threshold stimulus
15 impulse
16 triangular shape envelope
17 train
18 pulse
19 time with no stimulation
20 burst
21 constant shape envelope
22 biphasic envelope
23 first envelope
24 second envelope
25 rectangular envelope
26 magnetic flux density causing muscle contraction by rectangular envelope
27 increasing envelope
28 magnetic flux density causing muscle contraction by increasing envelope
29 coil
30 circuit wires
31 fastening point
32 blower
33 applicator
34 arrows
35 casing
36 outlet
37 connecting tube
38 conduit
39 switch
40 coil
41 energy storage device
42 energy source
43 protecting circuitry
44 coil
45 energy storage device
46 switch
47 energy source

GLOSSARY

Patient refers to any living organism, such as human or animal.

Stimulation refers to a magnetic flux density inducing an electric current in the biological structure.

Biological structure/target biological structure includes a cell, a neuron, a nerve, a muscle fiber, a tissue, a filament or an organ.

Neural structure includes at least one neural cell, a neuron, a neuroglia, a Schwann cell, a nerve, a neural tissue, spine or brain.

Biological response refers to any biological reaction based on the stimulation by time-varying magnetic field, such as membrane permeability change, depolarization or improved metabolism of the stimulated neural structure.

Neural system includes central neural system and/or peripheral neural system.

Central neural system (CNS) includes brain and/or spinal cord.

Muscle includes at least one of muscle fibre, muscle tissue or group, neuromuscular plate or nerve innervating the at least one muscle fibre.

Deep muscle refers to a muscle that is at least partly below superficial muscles and/or to the muscle that is covered by the thick layer of other tissue, e.g. mostly adipose tissue and/or the skin, with thickness 0.5, 1, 2, 3, 4, 5 or more centimeters.

Deep neural structure refers to hippocampus, hypothalamus, hypophysis or thalamus, subthalamic nucleus, globus pallidus externa or substantia nigra reticulata or any other.

Action potential interference refers to creating an action potential within the cell or modifying the time distribution of the action potential.

Impulse refers to the only one magnetic stimulus.

Pulse refers to a period of stimulation by time-varying magnetic field of at least one magnetic stimulus and time duration of no stimulation, i.e. time duration between two impulses from rise/fall edge to next rise/fall edge.

Repetition rate refers to frequency of firing the pulses; it is derived from the time duration of a pulse.

Induced energy refers to energy stimulating the target neural structure, the amount of induced energy corresponds to repetition rate, magnetic flux density and impulse duration.

Envelope refers to shape of induced energy stimulating the target neural structure, the envelope is perceived by the target neural structure as continuous stimulation.

Repetition frequency refers to frequency of repeating the envelope shape; it is derived from a period of an induced energy envelope.

Well-being refers to physical, mental and/or psychosomatic status of a patient when the patient is free of pain or ailment and feels healthy and/or happy.

Sensory-threshold stimulus is stimulation by magnetic flux density which induces sufficient current flow in the target biological structure when patient feels the very first perception of the induced current flow in the stimulated biological structure.

Motor-threshold stimulus is stimulation by magnetic flux density which induces sufficient current flow in the target biological structure at a level to begin to cause at least partial muscle contraction.

Noxious-threshold stimulus is stimulation by magnetic flux density which induces sufficient current flow in the target biological structure at a level which causes the patient to recognize first painful stimulus.

Below-sensory-threshold stimulus is stimulation by magnetic flux density that reaches sensory-threshold stimulus and is consequently slightly decreased after reaching the sensory-threshold stimulus.

Over-sensory-threshold stimulus is stimulation by magnetic flux density that reaches sensory-threshold stimulus and is consequently increased, however the motor-threshold stimulus is not reached.

Below-motor-threshold stimulus is stimulation by magnetic flux density that reaches motor-threshold stimulus and is consequently slightly decreased after reaching the motor-threshold stimulus.

Over-motor-threshold stimulus is stimulation by magnetic flux density that reaches sensory-threshold stimulus and is consequently increased, however the noxious-threshold stimulus is not reached.

Below-noxious-threshold stimulus is stimulation by magnetic flux density that reaches sensory-threshold stimulus and is consequently slightly decreased after reaching the sensory-threshold stimulus.

Over-noxious-threshold stimulus is stimulation by magnetic flux density that reaches sensory-threshold stimulus and is consequently increased.

DETAILED DESCRIPTION

Following the definition of World Health Organization, health is defined as a state of complete physical, mental and social well-being and not merely the absence of disease or infirmity. However, it seems to be that a state of complete physical, mental and social well-being corresponds rather to happiness than to health. The more appropriate definition of health is by Webster that is the state of being well, sound, or whole, in body, mind, or soul; especially, the state of being free from physical disease or pain.

Electric current is induced in the stimulated biological structure during magnet therapy. Distribution of magnetic field is uniform in the biological structure because water and biological molecules are diamagnetic substances. The magnetic field is not affected by diamagnetic substances. Therefore no loss of intensity or magnetic flux density occurs when passing through the biological structure or tissue. Even the scalp and skull are transparent to magnetic fields. Hence magnetic impulses may pass through these structures unimpeded. Particles (e.g. atoms, ions, molecules etc.) in the biological structures are influenced by the magnetic field and permeability of a cell membrane also increases.

An essential principle of magnet therapy used for biological structure stimulation is the influence of the magnetic field on the cell. The cell membrane is polarized due to the induced electric current. One of fundamental phenomenon of electric current in biological tissue may be an action potential occurrence, a transfer of neural excitation and/or a partial or full muscle contraction may be induced. Additionally, the effect of the generated action potential may modulate a painful stimulus transmission, providing a pain management effect. Furthermore, the action potential generation may be used for diagnostics or neural diseases treatment. Convenient repetition rates may cause pain alleviation and/or myorelaxation. Different repetition rates may cause muscle stimulation, and further different repetition rates may improve the patient's mental state.

A neuromuscular plate is stimulated causing an at least partial contraction of the muscle. The muscle is contracted at higher repetition rates and the contraction is stronger and more efficient for improving the muscle strength. The method is especially useful for deep muscles, major muscles, and for treatment of patients with high value of BMI. Deep muscle is the muscle underneath the superficial muscle. Muscle tissues may be selectively stimulated and the magnetic flux density of the stimulation may be adjusted based on patient characteristics or input.

With the present method muscle contractions induced by the applied magnetic flux density help to tone the muscle providing a more attractive appearance. As the muscle structure is stimulated by time-varying magnetic field the entire limb may be moved due to the high power of the magnetic stimulation signal. Nevertheless, the method is not limited to the applications to the limbs and the method is able to be applied to stimulation of any muscle, e.g. gluteus maximus or any muscle/deep muscle to induce body contouring and/or body shaping effect and fat burn. Additionally, shortened and/or flabby muscles are stretched. The physical fitness of the patient is improved as well. The muscle structures become toned with no need of any diet or spending time by exercising in fitness.

It is to be understood that the method is not limited to the particular applications and that the method may be practiced or carried out in various ways. The present methods may be used for treatment of major depressive disorder, epilepsy, schizophrenia, Parkinson's disease, Alzheimer's disease, Tourette's syndrome, amyotrophic lateral sclerosis, multiple sclerosis, attention deficit or hyperactivity disorder, obesity, bipolar disorder or mania, anxiety disorders, posttraumatic stress disorder, obsessive compulsive disorder, pain, migraine, chronic pain, neuropathic pain, rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spine injury & regeneration/rehabilitation, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, or eating disorders (bulimia, anorexia, binge eating).

The present invention relates to methods using stimulation of neural structure by time-varying magnetic field of magnetic flux density sufficient to induce at least action potential and/or active response of the neural structure. The broad spectrum of applications of biological structure stimulation by time-varying magnetic field is achieved due to high repetition rates and/or high value of magnetic flux density. Based on the repetition rate resolution the biological structure may be stimulated by envelope of suitable repetition frequency. Methods may be used for at least action potential generation and/or action potential modulation.

The applicator for magnet therapy includes at least one coil for generating time-varying magnetic field. The applicator may or may not include a magnetic core. The applicator is placed proximate to the patient's body and as the electric current flows in the coil the time-varying magnetic field is generated. The magnetic flux density is applied into the biological structure with or without the applicator contacting the skin. The electric current is induced and stimulates the target neural structure. Due to the stimulation at least action potential and/or a partial muscle contraction may occur.

The present method stimulates the neural structure by time-varying magnetic field defined by peak to peak magnetic flux density of at least 0.1 T, more preferably at least 0.5 T, even more preferably at least 1 T, even more preferably at least 1.5 T, most preferably at least 2 T, or up to 7 Tesla on the coil surface and/or repetition rate at least 50, 60, 70, 80, 90, 100, 120, 130, 140, 150, 180, 200, 250 or up to 700 Hertz with treatment/successive treatments lasting several seconds or longer, e.g. at least 5, 10, 30, 60, 120 or 240 seconds, or longer. The impulse duration is in the range of tens to hundreds of µs.

As shown in FIG. 1, stimulation of the biological structure, a cell, is explained by a curve 1 of an action potential. The action potential of the cell rapidly increases after the stimulus (induced by time-varying magnetic field) and reaches the threshold 2—so called depolarization. After reaching the maximal amplitude value, the membrane permeability changes and repolarization occurs. The negative value is reached in relation to resting potential 3. Afterwards the potential recharges back to the value of resting potential 3'. The time period from the threshold 2 to the return of potential to the threshold 2' (which equals threshold value 2) is called absolute refractory period 4. The cell is not able to be stimulated any more during the absolute refractory period 4, even by very strong stimulus. The time period from the end of absolute refractory period 4 to resting potential 3' is called relative refractory period 5. The cell is able to be stimulated only by the intensive over-threshold stimulus during the relative refractory period 5. Over-threshold stimulus is a stimulus of higher magnetic flux density than the value of threshold stimulus. The absolute refractory period 4 is the same time duration for all the cells, however, the relative refractory period 5 varies following the cell type.

Figure 2:
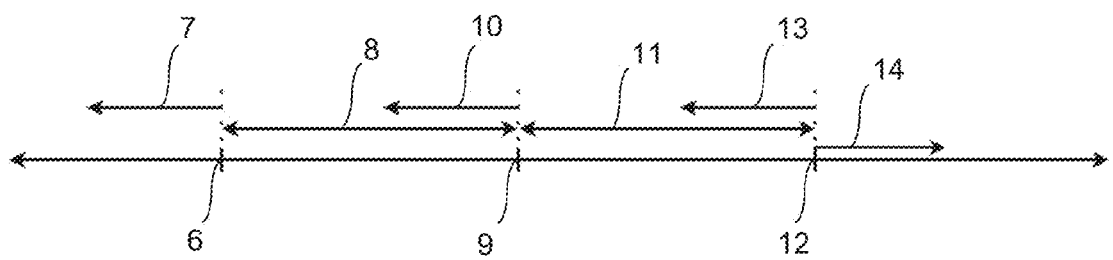
FIG. 2 illustrates a perceived intensity of the stimulus.

Referring to FIG. 2, following the perceived intensity of the stimulus the magnetic flux density may reach several values of stimulation. The magnetic flux density may induce sensory-threshold stimulus 6, below-sensory-threshold stimulus 7, over-sensory-threshold stimulus 8, motor-threshold stimulus 9, below-motor-threshold stimulus 10, over-motor-threshold stimulus 11, noxious-threshold stimulus 12, below-noxious-threshold stimulus; inducing the over-noxious-threshold stimulus 14 is not recommended. In general, the below-threshold stimulus is reached by inducing the threshold stimulus and consequently slightly decreasing the magnetic flux density. The over-threshold stimulus is reached by reaching the threshold stimulus and consequently slightly increasing the magnetic flux density. Therefore the situation may occur, that the value of magnetic flux density inducing the over-sensory-threshold equals to the value of magnetic flux density inducing the below-motor-threshold stimulus. Likewise the situation may occurs, that the value of magnetic flux density inducing the over-motor-threshold stimulus equals to the value of magnetic flux density inducing the below-noxious-threshold stimulus. Following the stimulation process the difference is that the magnetic flux density inducing the over-sensory-threshold stimulus/over-motor-threshold stimulus never reaches the motor-threshold stimulus/noxious-threshold stimulus.

According to one application of the invention, the envelope may be generated on the basis that the neural tissue can't distinct single pulses during the stimulation at higher repetition rates, e.g. exceeding 100 Hz, more preferably at least 150 Hz, even more preferably at least 200 Hz, most preferably at least 250 Hz, or up to 700 Hz. Generally, at least two pulses are necessary to create a simple shape of the envelope, e.g. rectangular or trapezoid. However, the more complex envelope shape is the more pulses are needed. The induced energy (IE) stimulating the target neural structure is a function of repetition rate, magnetic flux density and/or impulse duration. The repetition frequency of envelope is given by the envelope period, i.e. the envelope may include time with no stimulation as well. The envelope may be generated by several modulation approaches.

Figure 3A:
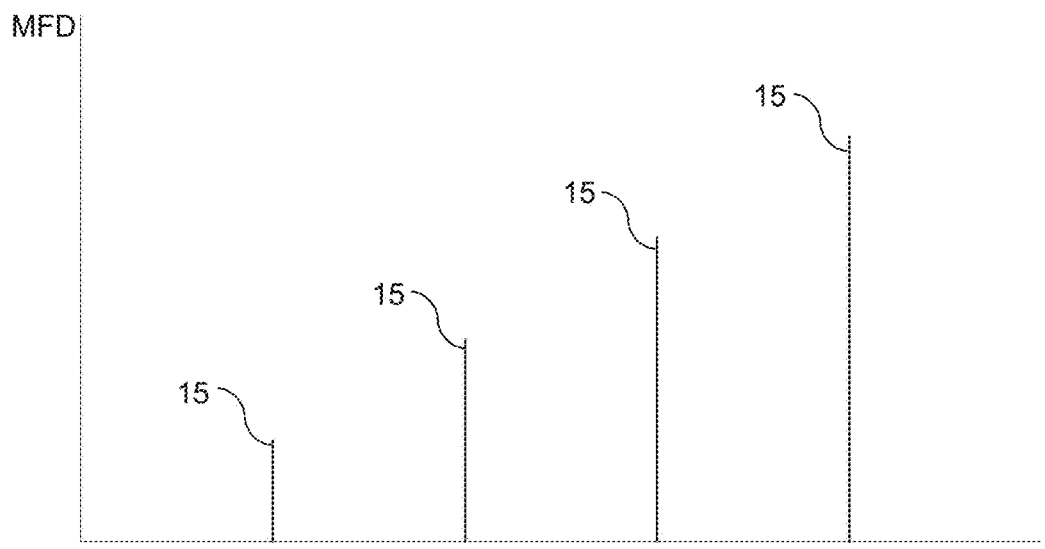
FIGS. 3a and 3b illustrate an envelope generation by magnetic flux density modulation.
Figure 3B:
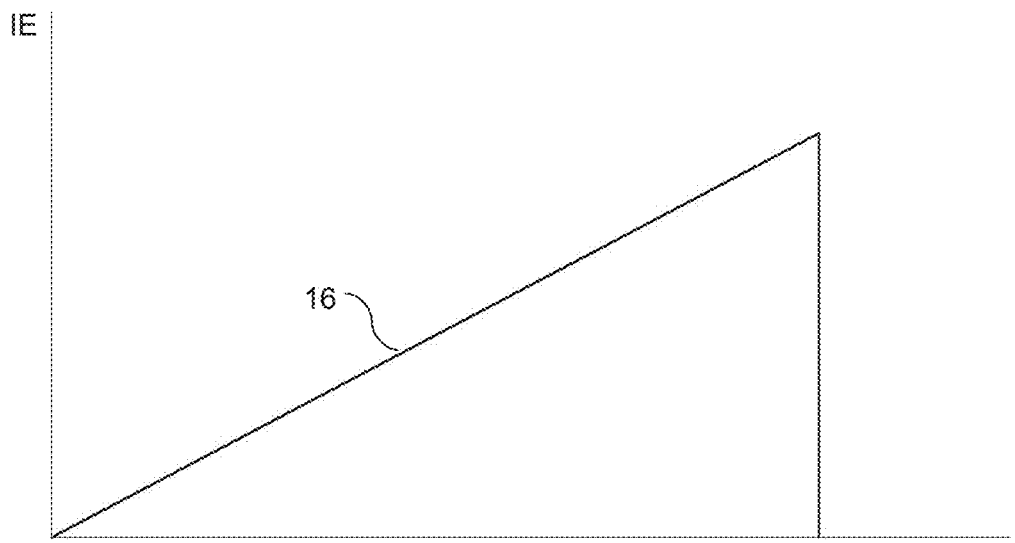

According to one aspect of application, envelope may be generated by time-varying magnetic field of varying peak magnetic flux density hence the process is called magnetic flux density modulation (MFDM). The principle of MFDM is described in FIGS. 3a and 3b. The repetition rate of the time-varying magnetic field is constant hence the period of the pulse is constant. The impulse duration remains constant as well. However, the magnetic flux density of each impulse 15 varies with respect to the preceding impulse 15, as in FIG. 3a. Therefore each impulse magnetic flux density is different from magnetic flux density of the preceding impulse. The principle is explained by triangular shaped envelope 16 as shown in FIG. 3b.

Figure 4A:
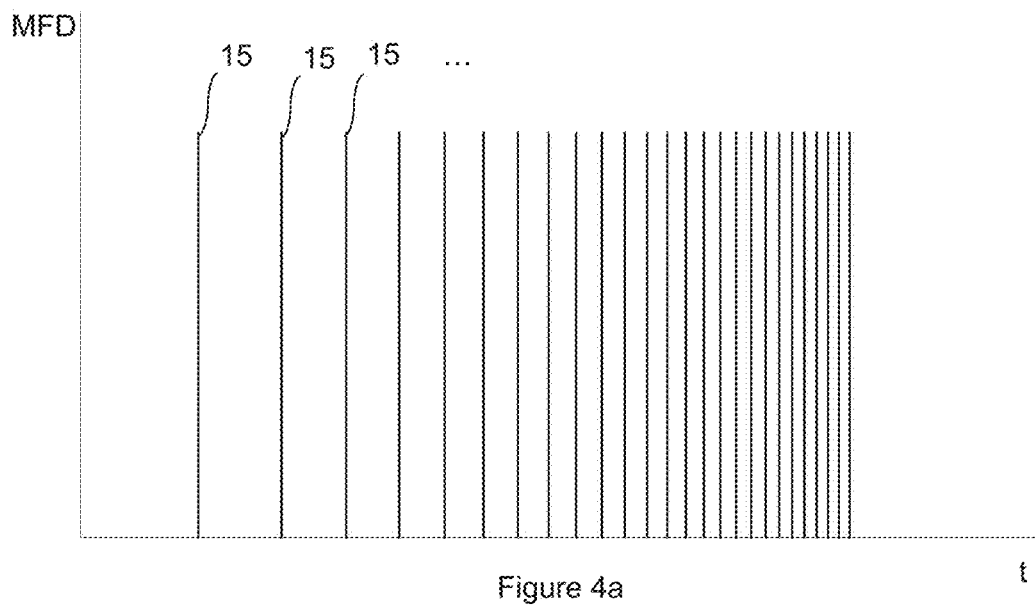
FIGS. 4a and 4b illustrate an envelope generation by repetition rate modulation.
Figure 4B:
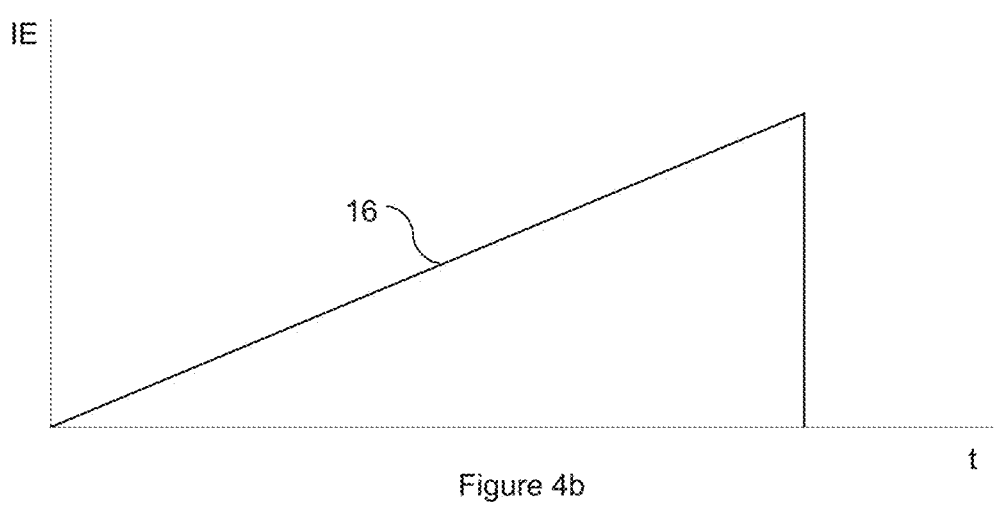

According to another aspect the application, envelope may be generated in repetition rate domain hence the process is called repetition rate modulation (RRM). The principle of RRM is described in FIGS. 4a and 4b. The magnetic flux density of each impulse 15 remains constants. The impulse duration remains constant as well. Therefore the induced energy for one pulse is constant. However, the repetition rate varies hence the time duration of each pulse varies with respect to the preceding pulse, see FIG. 4a. The actual value of induced energy corresponds to the actual repetition rate of the time-varying magnetic field. When the repetition rate increases the value of induced energy increases or vice versa. The principle is explained by triangular shaped envelope 16, see FIG. 4b.

Figure 5A:
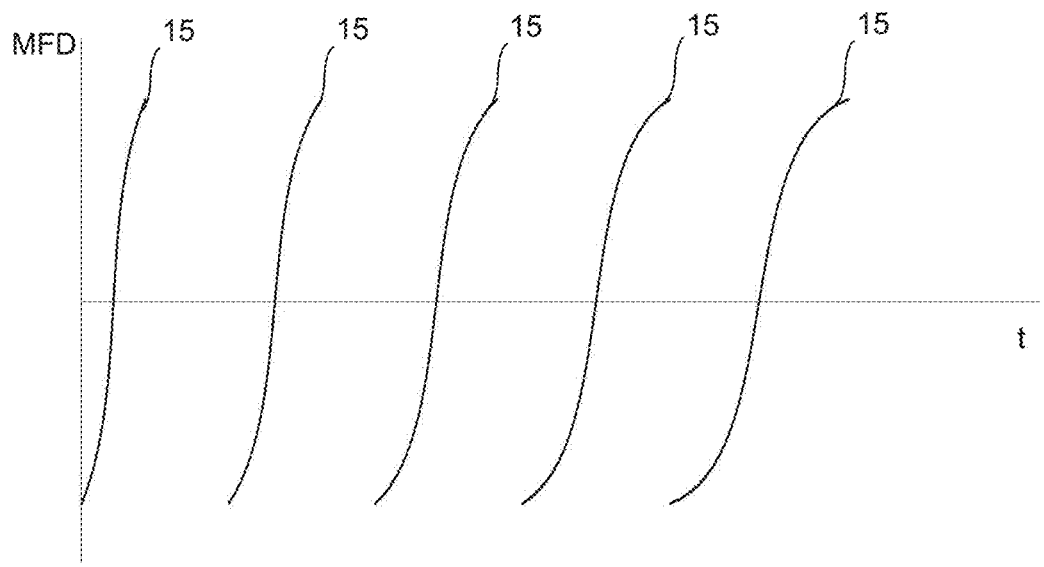
FIGS. 5a and 5b illustrate an envelope generation by impulse duration modulation.
Figure 5B:
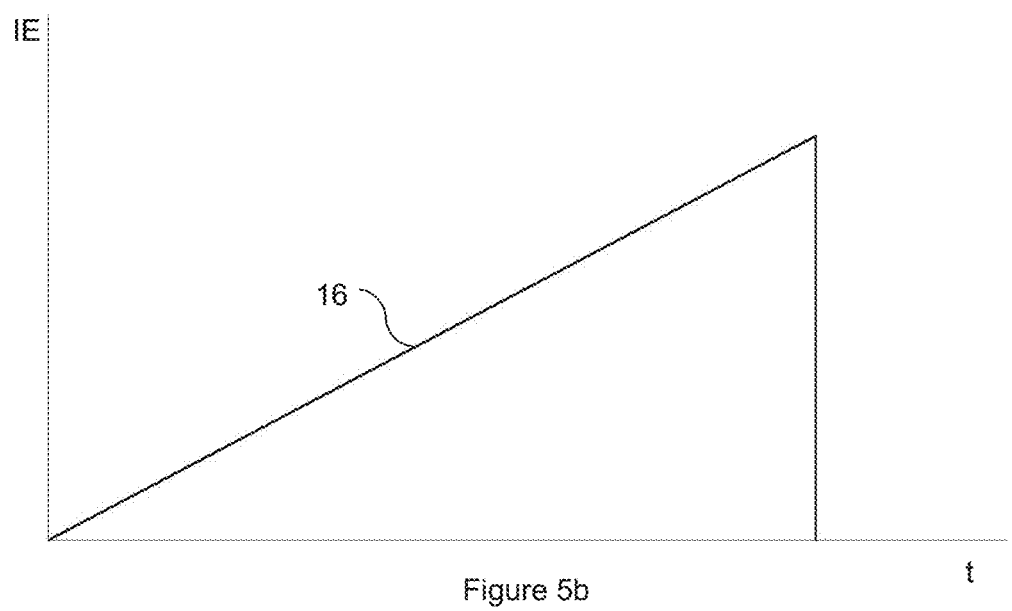

According to still another aspect of the application, envelope may be generated in impulse duration domain. The principle of impulse duration modulation is shown in FIGS. 5a and 5b where the magnetic flux density and the repetition rate of time-varying magnetic field remains constant. However, the impulse 15 duration of each pulse varies as shown FIG. 5a. The principle is explained by triangular shaped envelope 16 in FIG. 5b.

The modulation approaches are not limited by exemplary waveform. Therefore the envelope may be rectangular, square, saw-tooth, trapezoidal, sinusoidal, exponential etc. Person skilled in the art of neurology and/or physiotherapy may modulate various envelopes and/or envelopes combination.

The application is not limited to use the only single modulation approach. In the preferred application any combination of the upper mentioned approaches may be used.

Around 20% of the world's children and adolescents suffer for mental diseases or problems. About half of mental diseases begin before the age of 14. Similar types of diseases are being reported across cultures all over the world.

Over 800 000 people die due to suicide every year and suicide is the second leading cause of death in the patients in the age of 15-29. 75% of suicides occur in low- and middle-income countries. Neural diseases and use of alcohol contribute to many suicides around the world. Early identification and effective treatment are crucial to ensure that people receive the successful care they need.

According to another application of the invention, the neural structure stimulation by time-varying magnetic field may be used for treatment of psychiatric diseases. The successive repetition rate of the present method reaches at least 100 Hz, more preferably at least 110 Hz, most preferably at least 120 Hz. The magnetic flux density of the present treatment method exceeds at least 0.1 T, more preferably at least 0.5 T, even more preferably at least 1 T, most preferably at least 2 T or up to 7 T.

The method may be used for treatment of psychiatric diseases, such as e.g. depression, schizophrenia, migraine, depression, dyskinesias, Alzheimer's disease, Asperger's syndrome, Tourette's syndrome, attention-deficit hyperactivity disorder (ADHD), cognitive impairment, dementia, dystonia, restless legs, tremor, aphasia, ataxia or sphincter of Oddi disorders.

The applicator is placed in the proximity of the stimulated neural structure, e.g. brain, to focus the magnetic flux density to the targeted neural structure. The targeted neural structure is most commonly e.g. prefrontal cortex for alleviating the symptoms of depression or schizophrenia. However, person skilled in the art of neurology and/or physiotherapy may apply the stimuli to other locations which stimulation cause similar effect. Furthermore, the magnetic flux density and/or the repetition rate may be sufficient to induce at least action potential or even a partial seizure in the CNS.

The most commonly stimulated neural structure for migraine or headache treatment is trigeminal or occipital nerve. The trigeminal or occipital nerve stimulation is able to prevent and treat migraines.

The stimulation by time-varying magnetic field may also stimulate and/or temper the production of hormones, e.g. hypophysis hormones. However, person skilled in the art of neurology and/or physiology may apply the stimuli to other locations to influence the hormone production of other glands or visceral organs as well.

Additionally, the treatment of substance addiction may be promoted by the present method.

According to an alternative approach of the application for psychiatric diseases treatment, the neural structure may be stimulated by low repetition frequency envelope created by time-varying magnetic field of repetition rate exceeding 100 Hz, more preferably at least 150 Hz, even more preferably at least 200 Hz, most preferably at least 250 Hz, or up to 700 Hz. The repetition frequency may be up to 350 Hz, more preferably, up to 200 Hz, even more preferably up to 100 Hz.

According to another application of the invention, the neural structure stimulation by time-varying magnetic field may be used for treatment of neurodegenerative diseases and deep neural structure using repetition rates over 100 Hz, and a repetition rate of e.g., 130-160 Hz. However, the repetition rate may also exceed 200 Hz or 260 Hz, the repetition rate may reach up to 700 Hz. The impulse duration is in the range of 10 to 700 μs, more preferably in the range of 30 to 500 μs, even more preferably 50 to 250 μs, most preferably in the range of 60-90 μs. Magnetic flux density necessary for the effect of application is at least 0.1 T, more preferably at least 0.5 T, even more preferably 1 T, even more preferably at least 2.5 T, or up to 7 T.

The application of the invention may be used for treatment of neurodegenerative diseases, such as e.g. Alzheimer's disease, Parkinson's disease, Huntington's disease, Asperger's syndrome, Tourette's syndrome amyotrophic lateral sclerosis, depression, quadriplegia, paraplegia, dyskinesias, multiple sclerosis, attention-deficit hyperactivity disorder (ADHD), cognitive impairment, dementia, dystonia, restless legs, tremor, aphasia, ataxia, insufficient blood flow in the brain and many other diseases, disorders or syndromes. The stimulation by time-varying magnetic field is targeted to the damaged nerve or CNS to treat essential symptoms of the disease. The method may stimulate deep neural structures, e.g. brain structures. The effect of the stimulation may be similar to the effect of conventional invasive deep brain stimulation using implanted electrodes into the proximity of nucleus basalis of Meynert.

According to alternative approach of the application for neurodegenerative diseases treatment, the neural structure may be stimulated by low repetition frequency envelope created by time-varying magnetic field of repetition rate exceeding 100 Hz, more preferably at least 150 Hz, even more preferably at least 200 Hz, most preferably at least 250 Hz, or up to 700 Hz. The repetition frequency may be up to 350 Hz, more preferably, up to 200 Hz, even more preferably up to 100 Hz.

According to another aspect of the application for treatment of neurodegenerative diseases, the neural structure stimulation by time-varying magnetic field may be used for alleviating symptoms of e.g. Parkinson's disease. The neural structure may be stimulated by envelope of repetition frequency in the range of 40 to 60 Hz, more preferably in the range of 45 to 55 Hz, most preferably around 50 Hz. The magnetic flux density is sufficient to induce at least motor-threshold stimulus, more preferably at least over-motor-threshold stimulus. The treatment time may last for at least 20 minutes, more preferably at least 30 minutes, most preferably up to 60 minutes.

As the present methods for stimulation by time-varying magnetic field into deep neural structures are non-invasive, the disadvantages of surgery along with operative and postoperative risks for the patient are avoided.

According to another application of the invention, the neural structure stimulation by time-varying magnetic field may be used for neural system diagnostics. The neural structure may be stimulated by time-varying magnetic field generating various envelopes. The magnetic flux density of the present treatment method exceeds at least 0.1 T, more preferably at least 0.5 T, even more preferably at least 1 T, most preferably at least 2 T or up to 7 T.

According to one aspect of the application in neural system diagnostics, the neural structure may be stimulated by single pulses. The operator stimulates a patient by predefined different repetition rates to determine minimal magnetic flux density inducing at least partial muscle contraction for each repetition rate value. Feedback registering the at least partial muscle contraction may be e.g. visual, or by using technical device. Based on the measurement the graph of dependency of magnetic flux density and repetition rate may be compiled. The graph is very useful in the therapy planning.

In an alternative application the neural structure may be stimulated by rectangular or increasing shaped envelope as well.

According to another aspect of the application in neural system diagnostics, the neural structure may be stimulated by single pulses or rectangular shaped envelope, and by increasing shaped envelope. Both envelopes are used for determination of minimal magnetic flux density value sufficient to induce at least partial muscle contraction. The envelope duration may last 1 second. After the determination of both magnetic flux densities values, the level of muscle denervation may be calculated.

According to still another aspect of the application in neural system diagnostics, the neural structure may be stimulated in the at least one predefined location and in another predefined location the response of the stimulus may be measured. Hence the reaction time may be determined. In the preferred application, the time-varying magnetic field stimulates at the at least one predefined location on the arm and the recording device is placed on the hand. The recording device may be contact electrode or non-contact magnetic measuring device, e.g. superconducting quantum interference device. The feedback may be determined visually as well. The preferred repetition rate value for stimulation is in the range of 1 to 50 Hz and the impulse width is in the range of tens to hundreds of μs. In an alternative application the stimulation may be in predefined location, e.g. brain, and the feedback may be registered visually. It may be used planning neural surgery or during the surgery.

According to still another aspect of the application in neural system diagnostics, the neural structure may be stimulated during the maximal voluntary contraction. The additional contraction originating from stimulation by time-varying magnetic field is superposed. Several neural disorders may be determined, e.g. conduction deficiency, based on the determination of the additional muscle contraction strength. The contraction may be isometric, concentric or eccentric.

According to alternative aspect of the application in neural structure diagnosis, the neural structure may be stimulated by low repetition frequency envelope created by time-varying magnetic field of repetition rate exceeding 100 Hz, more preferably at least 150 Hz, even more preferably at least 200 Hz, most preferably at least 250 Hz, or up to 700 Hz. The repetition frequency may be up to 350 Hz, more preferably, up to 200 Hz, even more preferably up to 100 Hz.

Following the definition by World Health Organization, pain is defined as an unpleasant sensory or emotional experience associated with actual or potential tissue damage, or described in terms of such damage.

Pain may be caused by spastic and/or overtoned muscle, hence the myorelaxation effect may be cause analgesic effect as well.

According to still another application of the invention, the neural structure stimulation by time-varying magnetic field may be used for pain management. In general, the method is focused on neural structure stimulation by time-varying magnetic field of repetition rate at least 100 Hz and/or magnetic flux density sufficient to induce and/or modulate an action potential in a stimulated neural structure. The neural structure may be stimulated by at least repetition rate 100 Hz, more preferably at least 120 Hz, most preferably at least 140 Hz. The stimulation causes the pain alleviating effect. The principle is stimulation of neural structures which are able to transmit pain excitement. The purpose of the present stimulation by time-varying magnetic field is pain relief. The alternative effect may be a suppression of pain excitement transmission at different levels of receptors or CNS. Further, the higher repetition rate may include myorelaxative effect induced by short magnetic flux density impulses.

The application of the invention may be used for alleviation of e.g. back pain, Guillain Barre syndrome, diabetic polyneuropathy, dental procedure pain, knee osteoarthritis, anesthesia (pain relief during surgery), angina (chest pain from heart disease), ankylosing spondylitis, back pain, burn pain, cancer pain, chronic pain, dysmenorrhea (painful menstruation), headache, hemiplegia, hemiparesis (paralysis on one side of the body), labor pain, local anesthesia during gallstone lithotripsy, facial pain, trigeminal neuralgia, bruxism (tooth grinding) pain, myofascial pain, neck and shoulder pain, pain from broken bones, rib fracture or acute trauma, diabetic peripheral neuropathy, phantom limb pain, post-herpetic neuralgia (pain after shingles), irritable bowel syndrome, postoperative pain, post-stroke rehabilitation, rheumatoid arthritis, skin ulcers, temporomandibular joint pain, spinal muscular atrophy (in children), pain during hysteroscopy, carpal tunnel syndrome, soft tissue injury, intermittent claudication, knee replacement pain, achalasia, bursitis, esophageal spasm, fibromyalgia, fracture pain, herpes, hip pain, interstitial cystitis, joint pain, local anesthesia, menstrual cramps, muscle cramps, muscle spasticity, muscle strain or pain, musculoskeletal trauma, myofascial pain dysfunction syndrome, nerve damage, osteoarthritis, pain medication adjunct, pancreatitis, sacral pain, shingles, shoulder subluxation, sports injuries, thrombophlebitis, whiplash and neuralgias, central and peripheral neuropathic pain, spinal stenosis, sphincter of Oddi disorders or repetitive strain injuries.

Pain is transmitted by several types of pain conducting fibers differing by myelin sheath thickness and by the properties of the fiber. The magnetic flux density threshold of major vain fibers is written in Table 1

TABLE 1

| Fiber | Diameter | Myelin sheath thickness | Magnetic flux density threshold |
| --- | --- | --- | --- |
| Aα | Large | Large | Low |
| Aδ | Medium | Small | Medium |
| C | Small | No myelin | High |

There are several theories of pain management. Pattern theory premises that the pain excitement is transmitted from the peripheral receptor to the CNS in a pattern coded signal and the pain is interpreted by decoding the signal in CNS. Another pain management approach reveals gate-control theory based on a premise that the pain is transmitted through a "gate" in substantia gelatinosa in spinal dorsal horn wherein the large-diameter fibers block the "gate", whereas small-diameter fibers open the gate. Last pain management theory is called release of endogenous opioids based on the effect of endorphins, enkephalins and dynorphins. The secretion of these three endogenous opioids is activated by stimulation of Aδ- and C-fibers by low repetition rate time-varying magnetic field or by the low repetition rate envelope.

According to one aspect of the application in pain management, the neural structure may be stimulated by time-varying magnetic field at low repetition rate to cause pain management via stimulating central neural system or any part of it, e.g. anterior cingulate cortex or gyrus. The repetition rate may be at least several Hz, more preferably at least 10 Hz, even more preferably at least 20 Hz, even more preferably at least 50 Hz.

According to one approach of the aspect of the application in pain management, the neural structure may be stimulated by an envelope created by higher repetition rate values, e.g. exceeding 100 Hz, more preferably at least 150 Hz, even more preferably at least 200 Hz, most preferably at least 250 Hz, or up to 700 Hz. The envelope may be generated with predefined repetition frequency and/or shape. Furthermore, the neural structure, e.g. central neural system, may be stimulated by envelope at low repetition frequency at least 1 Hz, more preferably at least 2 Hz, even more preferably at least 5 Hz, even more preferably at least 10 Hz, even more preferably at least 200 Hz, or up to 350 Hz. The neural structure may be stimulated by various envelope shapes. The peak to peak magnetic flux density of the time-varying magnetic field may reach at least 0.1 T, more preferably at least 0.5 T, even more preferably at least 1 T, even more preferably at least 1.5 T, most preferably at least 2 T or up to 7 Tesla on the coil surface.

According to another aspect of the application in pain management, the neural structure may be stimulated by time-varying magnetic field at repetition rate in the range of 80 to 120 Hz, more preferably 90 to 110 Hz, even more preferably 95 to 105 Hz, most preferably around 100 Hz, with magnetic flux density inducing at least below-sensory-threshold stimulus or more preferably at least sensory-threshold stimulus following the application and indication. The method may stimulate the large diameter neural fibers. In general, time-varying magnetic field of repetition rate around 100 Hz with magnetic flux density inducing at least sensory-threshold stimulus is used preferably for pain relief effect. In a preferred application the magnetic flux density may induce the at least sensory-threshold stimulus and the time-varying magnetic field is modulated in the repetition rate range of 80 and 120 Hz. The method may be used for e.g. pain management in rheumatology or for treating post-traumatic states. In another preferred application the time-varying magnetic field repetition rate is at least 90 Hz, more preferably at least 100 Hz, even more preferably at least 110 Hz. The magnetic flux density may induce at least sensory-threshold stimulus, more preferably at least over-sensory-threshold stimulus to cause analgesic effect. The method may be used e.g. for chronic pain relief or Sudeck syndrome treatment amongst other.

In still another preferred application the method is used for treatment of phantom pain. The magnetic flux density may induce below-sensory-threshold stimulus. The treatment lasts at least 20 minutes, more preferably in the range of 25 to 30 minutes, or longer.

According to still another aspect of the application in pain management, the neural structure may be stimulated by time-varying magnetic field at sufficient magnetic flux density and at repetition rate up to 700 Hz, more preferably up to 500 Hz, most preferably up to 250 Hz to locally relief the pain and to enhance the patient comfort without taking pain killers or analgesics due to selected effect to nerve endings. The impulse duration is less than 1 ms, more preferably less than 800 µs, most preferably in the range of tens to hundreds of µs. The longer the impulse is the stronger subjective contraction intensity is perceived.

According to one approach of the aspect of the application in pain management, the neural structure may be stimulated in constant magnetic flux density manner by repetition rate in the range of 50 to 250 Hz, more preferably at least 100 Hz, most preferably at least 110 Hz and the pulse duration preferably at least 70 µs, more preferably at least 100 µs, most preferably at least 250 µs or up to 1000 µs. The magnetic flux density is sufficient to induce at least sensory-threshold stimulus, more preferably at least over-sensory-threshold stimulus. Quick adaptation to stimulus occurs during the stimulation in time therefore the magnetic flux density may be adjusted during the procedure following the patient's needs and perception. The method may be indicated for e.g. pain relief or for burns treatment.

According to another approach of the aspect of the application in pain management, the neural structure may be stimulated by a time-varying magnetic field to induce electric current of random repetition rate fluctuation around a predefined repetition rate. In the preferred application the repetition rate fluctuates at least 5%, more preferably at least 15%, most preferably at least 30% or up to 50%, the magnetic flux density is sufficient to induce at least sensory-threshold stimulus, more preferably at least over-sensory-threshold stimulus of the neural structure. The neural structure is not able to adapt for the stimulation by time-varying magnetic field since the repetition rate varies. Additionally, the magnetic flux density may be adjusted during the time. The method may provide analgesic effect.

According to still another approach of the aspect of the application in pain management, the neural structure may be stimulated by trains 17 of several pulses 18 and time with no stimulation after the train 17. The group of several pulses 18 and the time with no stimulation is called burst 20. Therefore one burst 20 consists of the only one train 17 and time with no stimulation 19. The train 17 preferably consists of at least 2 pulses, more preferably 5 pulses, even more preferably tens pulses or up to hundreds pulses; repetition rate of the pulses 18 is at least 100 Hz. The burst repetition rate may vary following the patient's needs. In the preferred application the burst repetition rate vary from 1 to 10 Hz. The number of pulses 18 in train 17 and/or the time with no stimulation may vary following the patient needs. The magnetic flux density is sufficient to induce at least motor-threshold stimulus, more preferably over-motor-threshold stimulus, even more preferably below-noxious-threshold stimulus.

Figure 6:
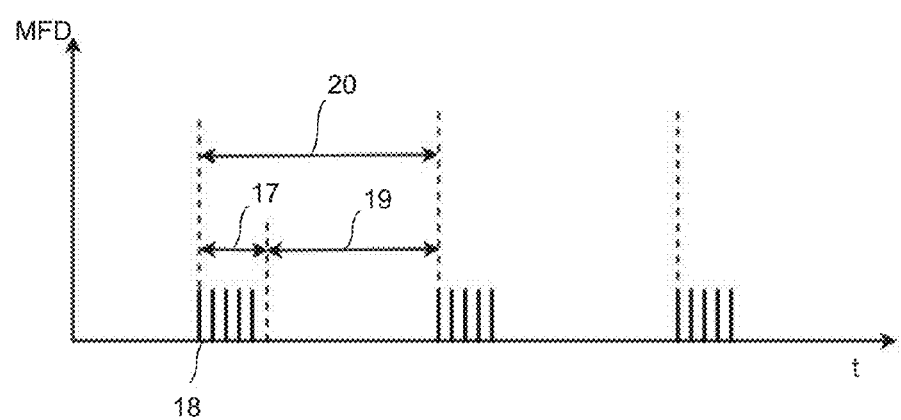
FIG. 6 illustrates a stimulation by exemplary clusters.

FIG. 6 shows an example of application of the stimulation by time-varying magnetic field with a repetition rate of 125 Hz in clusters 17 consisting of 5 pulses 18, with a burst 20 repetition rate 10 Hz. Total time duration of one burst 20 is 100 ms. Total stimulation time of one cluster 17 is 40 ms, hence the time with no stimulation 19 is 60 ms. The most important advantage of this approach is analgesic effect and almost no adaptation of the neural structure to the stimulation. The approach may be used e.g. for alleviating the acute pain.

The treatment program, envelope shape and magnetic flux density are indicated individually following the patient's needs and his/her subjective perception. The present method may be applicable for treatment of e.g. postoperative pain, labor pains, acute and chronic pain, neuralgia and neuropathia, musculoskeletal pains, sciatica, arthritis, knee or ankle pain, tendonitis, lower back pain, chronic headache, trigeminal pain, thalamic pain, causalgia, cancer pain, angina pectoris (reduces angina attacks and nitroglycerine consumption), metastatic bone pain, pain caused by burn injury, postoperative nausea, suprapubic or perineal pain, dysmenorrhea, postpartum pain, phantom pain, stump pain, anxiety, or for improving breath parameters via improving tidal inspiration volume and vital capacity etc.

According to still another aspect of the application in pain management, the neural structure may be stimulated by time-varying magnetic field at repetition rate in the range of 80 to 240 Hz, more preferably in the range of 100 to 200 Hz and by magnetic flux density inducing at least over-sensory-threshold stimulus, more preferably at least motor-threshold or over-motor-threshold stimulus inducing the at least partial muscle contraction, the noxious-threshold stimulus mustn't be induced. The stimulation may cause analgesic effect and the method may be used for treatment of e.g. causalgia, backbone pains, headache, migraine or thalamic, phantom or posttraumatic pains.

According to still another aspect of the application in pain management, the neural structure may be stimulated by time-varying magnetic field for alleviating the pain via spinal cord and/or spinal nerve stimulation. The aspect of the application may be based on the pattern theory of pain perception. The time-varying magnetic field may be delivered to the target area of backbone and/or spine. Specifically, the method exploits benefits and pain alleviating effect of stimulation with repetition rate at least 125 Hz, more preferably at least 135 Hz, most preferably around 145 Hz or up to 170 Hz. The magnetic flux density is sufficient to induce at least motor-threshold stimulus, more preferably below-noxious-threshold stimulus. Additionally, during the application at least partial muscle contraction may occur hence the local perfusion may increase. Still another benefit of the presented aspect may be myorelaxative effect, long lasting analgesic effect which may be used e.g. for alleviating pain after injuries, in orthopaedics, rheumatology, migraine, headache, neck pain, lumbago, pain of upper or lower extremities and improving the perfusion of itself. Furthermore, various pain syndromes may be treated by the present method.

According to still another aspect of the application in pain management, the neural structure may be stimulated by time-varying magnetic field at repetition rate of at least 160 Hz, more preferably at least 170 Hz, most preferably around 180 Hz, or up to 250 Hz. The present method may be based on gate-control theory of pain. In the preferred application the impulse duration lasts 500 µs at repetition rate around 180 Hz. Optimal magnetic flux density is sufficient to induce at least motor-threshold stimulus, more preferably below-noxious-threshold stimulus. The magnetic flux density may be adjusted following the patient's needs based on the sensitivity of a patient and the depth of the stimulated neural structure. However, the minimal magnetic flux density exceeds 0.1 T, more preferably 0.5 T, even more preferably 1 T, most preferably up to 7 T to induce the at least one action potential. Benefit of the present method is myorelaxative effect. The stimulated location may be situated over the backbone, e.g. over cervical, thoracic, lumbar and sacral regions. Several stimulation positions are established to alleviate a pain in different locations or extremities. The most significant usage may be for alleviating chronic pain, pain originating from coxarthrosis or gonarthrosis, posttraumatic states or rheumatic pain.

According to still another aspect of the application in pain management, the neural structure may be stimulated by time-varying magnetic field at repetition rate at least 180 Hz, more preferably at least 200 Hz, even more preferably up to 240 Hz for alleviating the pain caused by e.g. causalgia, backbone pains, headache, migraine or thalamic, phantom or posttraumatic pains. The magnetic flux density is sufficient to induce at least motor-threshold stimulus and then the stimulation may continue up to below-noxious-threshold stimulus.

According to still another aspect of the application in pain management, the neural structure may be stimulated by envelope at lower repetition frequencies, e.g. below 100 Hz. Therefore the time-varying magnetic field repetition rate reaches the higher values, e.g. exceeding 100 Hz, more preferably at least 150 Hz, even more preferably at least 200 Hz, most preferably at least 250 Hz, or up to 700 Hz in order to generate the envelope with repetition frequency up to 350 Hz, more preferably, up to 200 Hz, most preferably below 100 Hz.

Figure 7A:
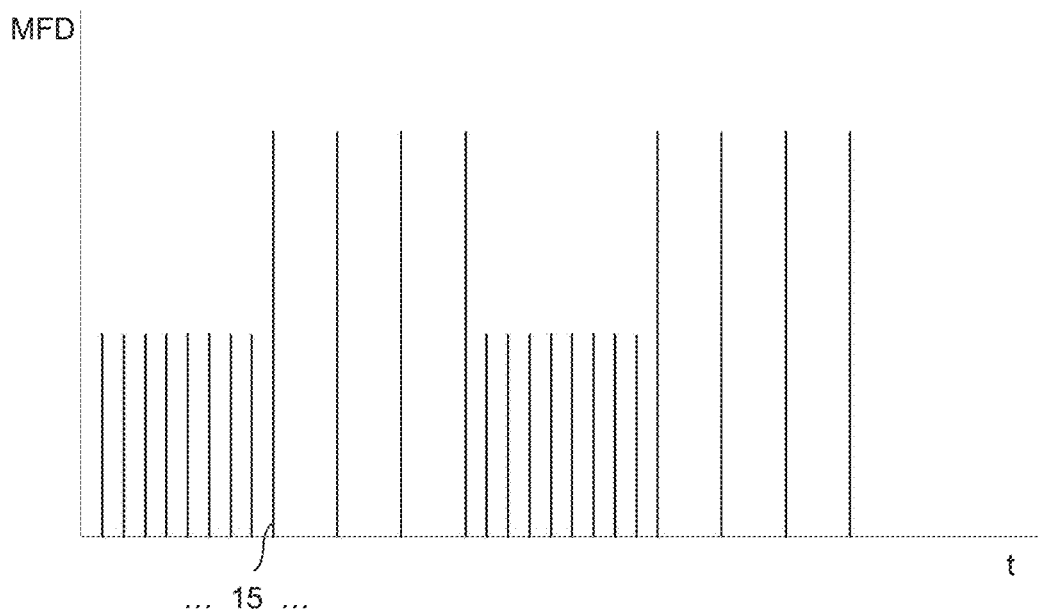
FIGS. 7a and 7b illustrate a generation of constant envelope.
Figure 7B:
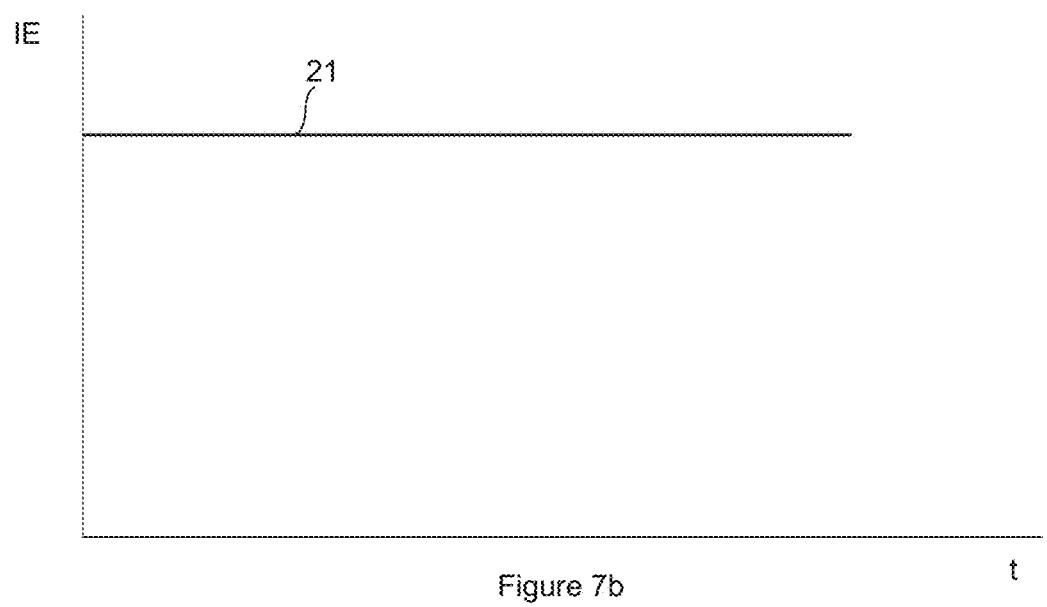

According to one approach of the aspect of the application in pain management, the neural structure may be stimulated by the high repetition rate time-varying magnetic field. The envelope 21 remains constant, see FIG. 7b, and may cause analgesic effect. The constant envelope 21 may be generated by e.g. constant repetition rate and magnetic flux density and impulse duration, or any combination of modulation approaches, e.g. varying magnetic flux density and repetition rate (see FIG. 7a). The magnetic flux density is sufficient to induce at least sensory-threshold stimulus, more preferably at least over-sensory-threshold stimulus, most preferably at least motor-threshold stimulus. The method may be used for alleviating a pain caused by neuropathy, neuralgia, or for innervation deficiency treatment, treatment of paresis or plegia. Additional effects may be improved metabolism or perfusion. The perfusion diseases may be treated as well, e.g. Raynaud's syndrome.

According to another approach of the aspect of the application in pain management, the neural structure may be stimulated by high repetition rate time-varying magnetic field generating low repetition frequency envelope up to 20 Hz, more preferably in the range of 1 to 15 Hz, most preferably in the range of 2 to 10 Hz. The magnetic flux density is sufficient to induce at least below-sensory-threshold stimulus, more preferably at least sensory-threshold stimulus, even more preferably motor-threshold stimulus or even noxious-threshold stimulus. The target neural structures are large diameter neural fibers in the case of lower magnetic flux densities. In the case of higher magnetic flux densities the target neural fibers are small diameter fibers. The impulse duration is at least 100 µs, more preferably at least 300 µs, even more preferably at least 500 µs or up to 1000 µs. The stimulation of small diameter fibers induces the increase of secretion of endogenous endorphins.

According to still another approach of the aspect of the application in pain management, the neural structure may be stimulated by high repetition rate time-varying magnetic field generating low repetition frequency envelope in the range of 20 to 40 Hz, more preferably around 30 Hz. The magnetic flux density is sufficient to induce at least below-sensory-threshold stimulus, more preferably at least sensory-threshold stimulus, the repetition frequency remains preferably constant. The approach may be applied for pain alleviation in rheumatology or posttraumatic states.

Figure 8A:
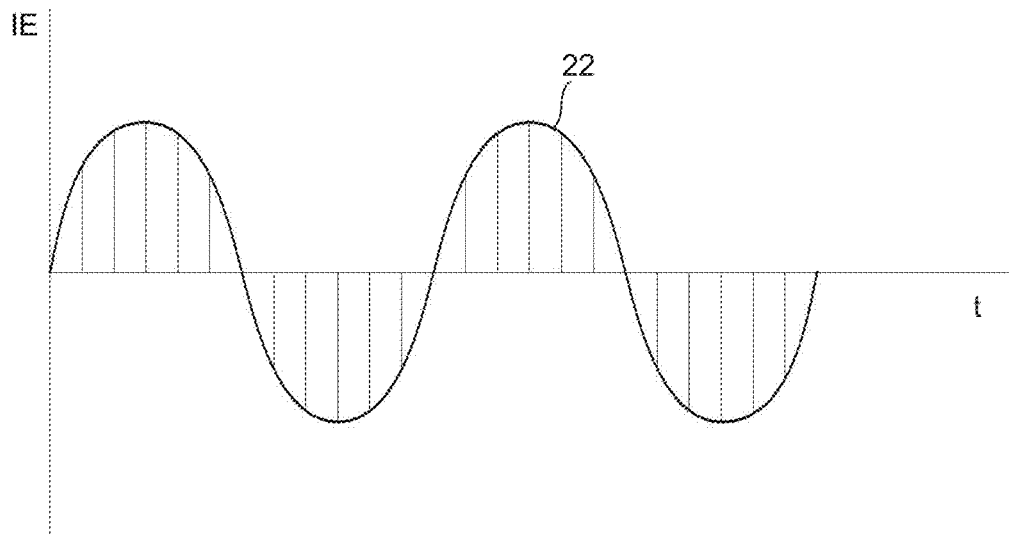
FIGS. 8a, 8b and 8c illustrate a generation of FSE and SSE from OS.

According to still another approach of the aspect of the application in pain management, the neural structure may be stimulated by monophasic envelope or by different wave rectification of biphasic envelope 22 (BE) as shown in FIG. 8a.

The first envelope 23 (FE) is half-wave rectified BE 22. Therefore the repetition frequency of FE 23 is the same as the repetition frequency of the original BE 22. Further, FE 23 includes magnetic stimulation for the same time duration as the original BE 22, the second time duration of the period is no stimulation, e.g. the FE 23 includes half-period of sinusoidal and second half-period with no stimulation in the case of symmetric BE 22 (see FIG. 8b). The effect of FE 23 may be rather stimulating, toning or excitatory. However, it may cause analgesic effect by magnetic flux density sufficient to induce at least below-sensory-threshold stimulus, more preferably at least motor-threshold stimulus.

The second envelope 24 (SE) is full-wave rectified BE 22. SE 24 includes magnetic stimulation for entire period. Therefore, in the case of symmetric BE 22 the repetition frequency of SE 24 is double repetition frequency of the original BE 22. (see FIG. 8c). The SE 24 effect may be rather inhibitory, e.g. analgesic or relaxation. Following the pain alleviating effect the muscle contraction is not painful during the increased magnetic flux density of the time-varying magnetic field. The both envelopes, FE and/or SE, may be superposed on the constant envelope (CE) inducing at least below-sensory-threshold stimulus. The superposition of CE and FE and/or SE may induce at least sensory-threshold stimulus, more preferably at least motor-threshold stimulus.

FE and/or SE may be combined in one treatment. The ratio of FE and SE may vary as well. The amplitude and/or repetition frequency of both envelopes may vary as well.

The present approach is contactless and may be used over the painful joints, paravertebrally, over Head areas, over the painful point, according to the nerve, over the organ or muscle.

The present approach may be applied e.g. for treatment of pain, neuralgia, arthrosis pain, spondylosis, periarthritis, epicondylitis, myalgia, lumbago, torticollis, posttraumatic states, Raynaud's disease, Sudeck's syndrome, varicosities or pain in abdominal region.

According to still another approach of the aspect of the application in pain management, the neural structure may be stimulated by various envelopes. The envelope repetition frequency is in the range of 40 to 120 Hz, more preferably in the range of 50 to 100 Hz. The magnetic flux density reaches sufficient value to induce at least below-sensory-threshold stimulus, more preferably at least sensory-threshold stimulus, even more preferably over-sensory-threshold stimulus. The impulse duration is at least 20 µs, more preferably at least 50 µs, even more preferably at least 100 µs, most preferably up to several hundreds of µs. The treatment duration may be at least 20 minutes or up to 60 minutes.

According to still another approach of the aspect of the application in pain management, the neural structure may be stimulated by envelope generated by two repetition rates interference. The first repetition rate may differ from the second repetition rate. In the exemplary embodiment the first repetition rate may be 500 Hz and the second repetition rate may be 490 Hz. The interference of the two repetition rates generates envelope of repetition frequency given by the repetition rate difference hence the interference stimulation repetition frequency may be 10 Hz in the exemplary application.

The effect of the modulated repetition frequency in the range up to 10 Hz may cause pain relief effect by selective application the time-varying magnetic field to the neural structures, e.g. C-fibers. The effect of the stimulation may increase the opioid generation to relief the pain. In alternative application the modulated time-varying magnetic field repetition frequency may be around 100 Hz, e.g. in the range of 80 to 120 Hz, more preferably in the range of 90 to 110 Hz. The higher value of repetition frequency induces spasmolytic effect. The repetition frequency in the range of 85 to 105 Hz, more preferably in the range of 90 to 100 Hz may be used to spasmolytic stimulation of spastic muscles, in the preferred application the repetition frequency may vary. In another preferred application the repetition frequency is constant around 100 Hz, the application may be used for treatment of e.g. spastic obstipation.

The advantages of the present methods compared to conventional electrotherapy methods are: non-invasive and contactless application; high rate of treatment acceptability by a patient; elimination of electrotherapeutic side-effect such as heat production in proximity of the stimulation electrode; and low neural structure stimulation adaptability for these aspects of the application.

According to still another application of the invention, the neural structure stimulation by time-varying magnetic field may be used for myorelaxation. The neural structure may be stimulated by at least repetition rate at least 100 Hz, more preferably at least 110 Hz, even more preferably at least 120 Hz, most preferably 130 Hz. The neural structure may be stimulated by various time-varying magnetic field shapes. The magnetic flux density may be sufficient to cause at least motor-threshold stimulus and at least partial muscle contraction. In general, the myorelaxation effect may be reached by higher repetition rates and/or relatively short impulse duration in the range of tens to several hundreds of µs.

The application of the invention may be used for treatment of e.g. postoperative ileus (bowel obstruction), overactive bladder, Guillain Barre syndrome, quadriplegia, paraplegia, dyskinesias, paresthesias, knee osteoarthritis, anesthesia (pain relief during surgery), bruxism (tooth grinding) pain, myofascial pain, neck and shoulder pain, irritable bowel syndrome, temporomandibular joint pain, spinal muscular atrophy (in children), chronic obstructive pulmonary disease rehabilitation, achalasia, bursitis, esophageal spasm, fibromyalgia, menstrual cramps, muscle cramps, muscle spasticity, muscle strain or pain, musculoskeletal trauma, myofascial pain dysfunction syndrome, sacral pain, thrombophlebitis, central and peripheral neuropathic pain, spinal stenosis, repetitive strain injuries or detrusor instability.

According to one aspect of the application in myorelaxation, the neural structure may be stimulated by higher repetition rates over 100 Hz. The neural structure stimulation may be focused on e.g. spastic muscle and its trigger point. Proposed stimulation may enable muscle hypertonia alleviation of the overloaded muscle fibers to relieve a local spasm. Similarly it may stimulate the muscle insertion or muscle group as well.

According to the one approach of the aspect of the application in myorelaxation, the stimulation by time-varying magnetic field may be divided into two separate periods, where the neuromuscular plate is stimulated by time-varying magnetic field during the first period. The magnetic flux density is sufficient to induce at least motor-threshold stimulus to cause at least partial muscle contraction in the stimulated biological structure. The muscle is activated by isometric contraction by repetition rate below 100 Hz and sedation follows. The most reactive fibers are selectively inhibited. During the second period the repetition rate is increased to at least 100 Hz, 150 Hz, or 200 Hz. The muscle is relaxed due to high repetition rate. The method is used for high-quality relaxation of at least one muscle fiber.

According to another aspect of the application in myorelaxation, the neural structure may be stimulated by higher repetition rates in the range of 150 to 210 Hz, more preferably in the range of 165 to 195 Hz, even more preferably in the range of 175 to 185 Hz, most preferably around 180 Hz. The magnetic flux density is sufficient to induce at least over-sensory-threshold stimulus, more preferably motor-threshold, even more preferably over-motor-threshold stimulus. The impulse duration is at least tens of μs, more preferably at least 250 μs, most preferably at least 500 μs. The time duration of a pulse may be at least 1 ms, more preferably at least 2.5 ms, most preferably around 5.5 ms. A temporary reflex adjustment of at least one hypertonic muscle fiber or muscle or muscle groups may be achieved by the application of time-varying magnetic field, thereafter myorelaxation effect may be provided.

According to still another aspect of the application in myorelaxation, the neural structure may be stimulated by time-varying magnetic field at repetition rate in the range of 150 to 250 Hz. The magnetic flux density is sufficient to induce at least over-sensory-threshold stimulus, more preferably motor-threshold, even more preferably over-motor-threshold stimulus According to one approach of the aspect of the application in myorelaxation, the neural structure may be stimulated by time-varying magnetic field at repetition rate in the range of 160 Hz to 200 Hz, even more preferably in the range of 170 Hz to 190 Hz, even more preferably in the range of 175 to 185 Hz, most preferably around 180 Hz.

According to another approach of the aspect of the application in myorelaxation, the neural structure may be stimulated by time-varying magnetic field at repetition rate in the range of 175 to 225 Hz, even more preferably in the range of 180 to 220 Hz, most preferably around 200 Hz. In a preferred application the time-varying magnetic field at repetition rate 200 Hz is constant containing no modulation.

According to still another approach of the aspect of the application in myorelaxation, the neural structure may be stimulated by time-varying magnetic field at repetition rate up to 250 Hz, more preferably up to 235 Hz, even more preferably up to 225 Hz, most preferably up to 220 Hz.

According to still another aspect of the application in myorelaxation, the neural structure may be stimulated by envelope at lower repetition frequencies, e.g. below 100 Hz. Therefore the time-varying magnetic field repetition rate reaches the higher values, e.g. exceeding 100 Hz, more preferably at least 150 Hz, even more preferably at least 200 Hz, most preferably at least 250 Hz, or up to 700 Hz in order to generate the envelope with repetition frequency up to 350 Hz, more preferably, up to 200 Hz, most preferably below 100 Hz.

According to one approach of the aspect of the application in myorelaxation, the neural structure may be stimulated by envelope of repetition frequency range up to 100 Hz, more preferably up to 50 Hz, most preferably up to 30 Hz. The magnetic flux density is sufficient to induce at least over-sensory-threshold stimulus, more preferably motor-threshold, even more preferably over-motor-threshold stimulus According to one approach of the aspect of the application in myorelaxation, the neural structure may be stimulated by time-varying magnetic field at repetition rate in the range of 30 to 150 Hz, more preferably in the range of 50 to 100 Hz. The time-varying magnetic field is preferably modulated to prevent the neural structure to adapt the magnetic stimulation. The magnetic flux density is sufficient to induce at least over-sensory-threshold stimulus, more preferably motor-threshold, even more preferably over-motor-threshold stimulus All the mentioned aspects of the application of the invention causing myorelaxation effect may also include analgesic effect. However, the patient may perceive different subjective intensity of analgesic effect for the specific aspects of the application of the invention.

The application of the invention may be also used in sport medicine for stretching of athletes before a performance and muscle relaxation after the performance, thereafter it significantly contributes to muscle regeneration. Further applications are treating for muscle imbalance or muscle relaxation caused by overload, pain relief or elimination and preparation the muscle for physical activity.

According to still another application of the invention, the neural structure stimulation by time-varying magnetic field may be used for causing stimulation effect. The neural structure may be stimulated by the envelope hence the repetition rate exceeds 100 Hz, more preferably at least 150 Hz, even more preferably at least 200 Hz, most preferably at least 250 Hz or up to 700 Hz. The envelope may be generated with predefined repetition frequency. Further, neural structure may be stimulated by low repetition frequency envelope to induce at least motor-threshold stimulus and at least partial muscle contraction occurs. The magnetic flux density of the present treatment method exceeds at least 0.1 T, more preferably at least 0.5 T, even more preferably at least 1 T, most preferably at least 2 T or up to 7 T. In an alternative application of the invention the stimulation effect may be caused by stimulating CNS.

The application of the invention may be used for muscle stimulation in general, however, the application may be used for treatment of e.g. urinary incontinence, fecal incontinence, Guillain Barre syndrome, quadriplegia, paraplegia, hemiplegia, hemiparesis (paralysis on one side of the body), post-stroke rehabilitation, spinal cord injury, spinal muscular atrophy (in children), gastroparesis, chronic obstructive pulmonary disease rehabilitation or spinal stenosis as well. The application of the invention may also improve the breath parameter such as tidal inspiration volume.

According to one aspect of the application in muscle stimulation, the at least partial muscle contraction may be caused by neural structure stimulation at low repetition rate via stimulation of central neural system or any part of it, e.g. brain or motor cortex. The repetition rate may be at least several Hz, more preferably at least 10 Hz, even more preferably at least 20 Hz, even more preferably at least 30 Hz, most preferably at least 50 Hz. The magnetic flux density may reach at least 0.002 T, more preferably at least 0.1 T, even more preferably at least 1 T, most preferably at least 2 T, or up to 7 T.

According to another approach of the aspect of the application in pain management via CNS stimulation, the neural structure may be stimulated by envelope at lower repetition frequencies, e.g. at least 1 Hz, more preferably at least 2 Hz, even more preferably at least 5 Hz, even more preferably at least 10 Hz, or up to 350 Hz. Therefore the time-varying magnetic field repetition rate reaches the higher values, e.g. exceeding 100 Hz, more preferably at least 150 Hz, even more preferably at least 200 Hz, most preferably at least 250 Hz, or up to 700 Hz in order to generate the envelope.

The aspect of the application in muscle stimulation may have great benefit in treatment of motoric and/or mobility dysfunctions, e.g. the treatment may accelerate recovery after stroke.

According to another aspect of the application in muscle stimulation, the neural structure may be stimulated by envelope of repetition frequency up to 10 Hz, more preferably in the range of 0.5 to 5 Hz. The low repetition frequency may cause the stimulation effect to smooth muscle. The application is beneficial for treatment of digestive diseases, e.g. obstipation.

According to still another aspect of the application in muscle stimulation, the neural structure may be stimulated by envelope of repetition frequency in the range of 20 to 40 Hz, more preferably in the range of 25 to 35 Hz, most preferably around 30 Hz. The pulses are formed in trains of duration up to hundreds of ms, more preferably up to 500 ms, even more preferably in the range of 40 to 400 ms. The application may be useful for stimulation of patients suffering for hemiplegia.

According to still another aspect the application in muscle stimulation, the neural structure may be stimulated by increasing envelope. Denervated muscle lacks the ability of voluntary contraction due to a lesion or nerve degradation caused by e.g. polio or trauma, so that the signals from the central neural system are not received. The muscle loses the ability of contraction and/or flexibility and it atrophies. Effects of muscle atrophy are significant just after three weeks of inactivity. Due to ineffective muscle contraction the function of the denervated muscle is performed by the synergist muscles. Therefore the synergists are overloaded and many dysbalances may occur. Additionally, the overloaded muscle become tough and hard and pain may occur as well. The present method provides contactless method for prevention and treatment of muscle dysbalances caused by denervated muscle.

Figure 9:
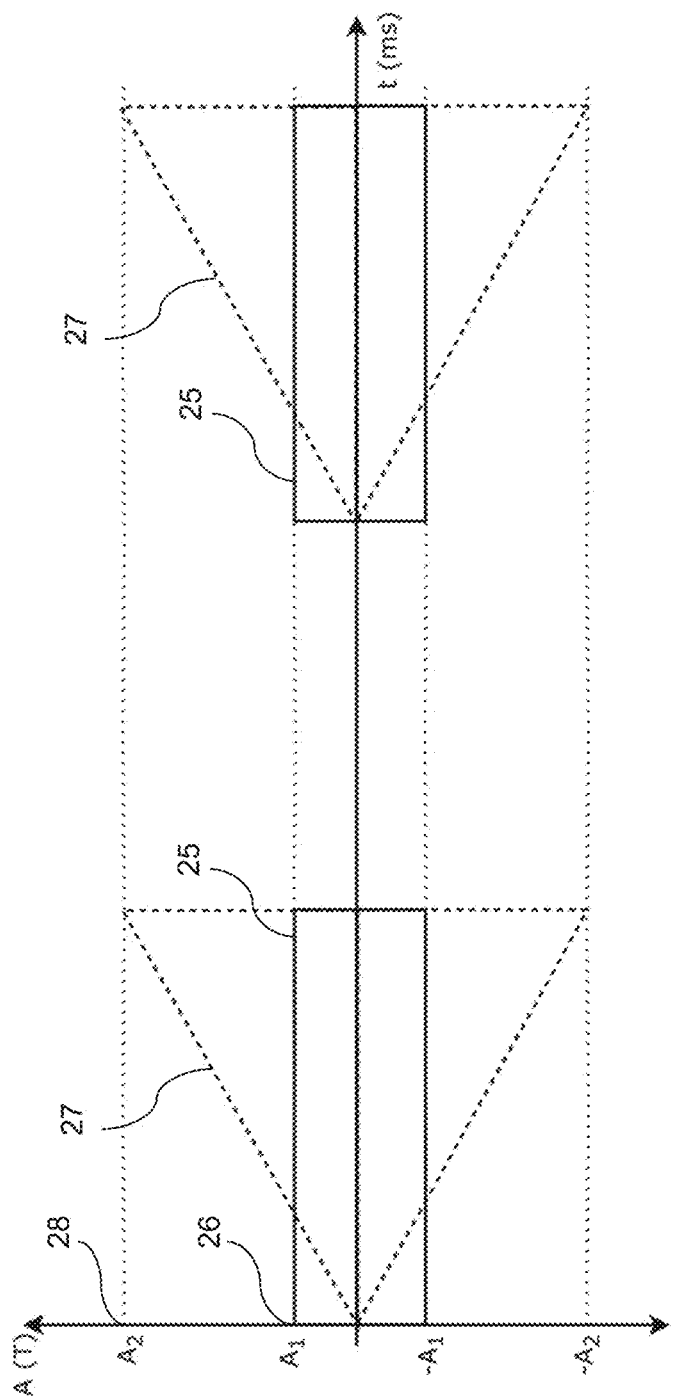
FIG. 9 illustrates a threshold value corresponding to different envelopes of the stimulation signal

The stimulation of denervated muscle is based on the adaptability of health motor unit for the raising magnetic flux density. Denervated muscle lacks an ability of adaptation to raise induced electric stimulus as normal healthy muscle. As seen in FIG. 9, when the healthy muscle is stimulated by a rectangular envelope 25 the muscle contraction may occur at magnetic flux density $A_1$ 26. When the healthy muscle is stimulated by increasing envelope 27 the muscle contraction may occur at magnetic flux density value $A_2$ 28. However, when the denervated muscle is stimulated by increasing envelope 27 the denervated muscle contraction may occur at magnetic flux densities below $A_2$ 28. Magnetic flux density value $A_2$ 28 is multiplication of magnetic flux density value $A_1$ 26, wherein the multiplication coefficient is positive number greater than 1.

The stimulation results in an at least partial contraction of denervated muscle and the contraction of healthy muscle is eliminated or minimized.

According to one approach of the aspect of the application in muscle stimulation, the neural structure may be stimulated by the increasing or triangular envelope of repetition frequency in the range of 25 to 65 Hz, more preferably in the range of 35 to 55 Hz, even more preferably in the range of 40 to 50 Hz, most preferably around 45 Hz. In an alternative application the period may include a time with no stimulation, however, the repetition frequency of complete envelope remains as mentioned before. The method may be used for stimulation of denervated muscle structure in advance.

According to still another aspect of the application in muscle stimulation, the neural structure may be stimulated by envelope of repetition frequency in the range of 20 to 80 Hz, more preferably in the range of 30 to 70 Hz, most preferably in the range of 40 to 60 Hz. An application may e.g. use repetition rate at least 35 Hz, more preferably at least 40 Hz, most preferably at least 45 Hz, the envelope may be rectangular. The stimulation may be used for e.g. muscle exercising and/or strengthening or muscle reeducation after injuries. Another application may be used for muscle fatigue testing. In another application the envelope repetition frequency is at in the range of 40 to 60 Hz, more preferably in the range of 45 to 55 Hz, most preferably around 50 Hz. In the most preferred application the envelope is rectangular shaped and lasts for 10 ms with 10 ms time of no stimulation.

According to still another aspect of the application in muscle stimulation, the neural structure may be stimulated by monophasic envelope or by different wave rectification of biphasic envelope 22 (BE) as shown in FIG. 8a.

Figure 8B:
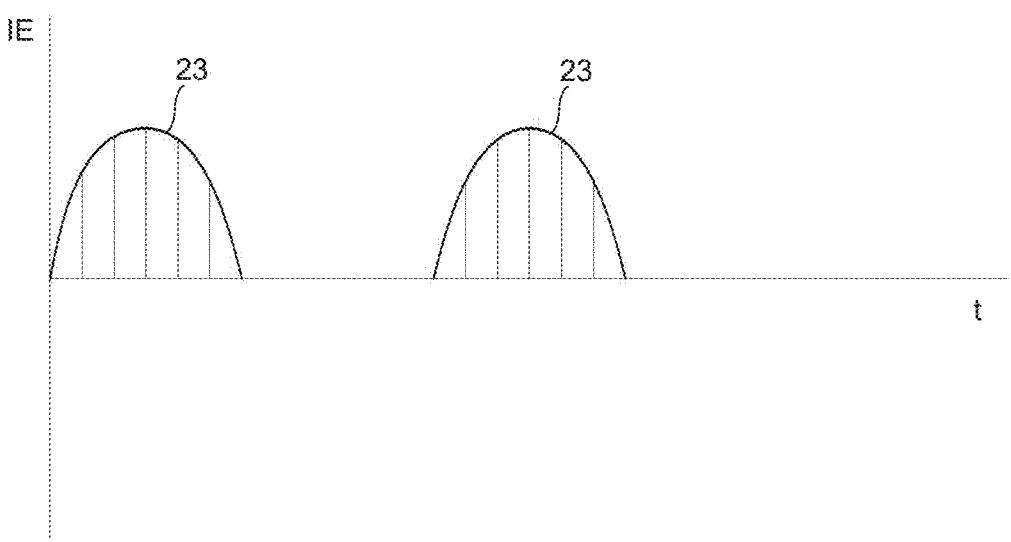
Figure 8C:
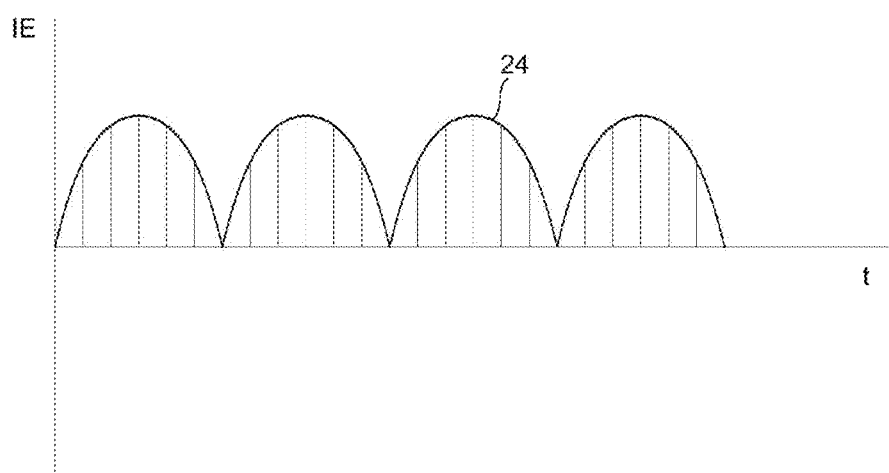

The first envelope 23 (FE) is half-wave rectified BE 22. Therefore the repetition frequency of FE 23 is the same as the repetition frequency of the original BE 22. Further, FE 23 includes magnetic stimulation for the same time duration as the original BE 22, the second time duration of the period is no stimulation, e.g. the FE 23 includes half-period of sinusoidal and second half-period with no stimulation in the case of symmetric BE 22 as shown in FIG. 8b. The effect of FE 23 may be rather stimulating, toning or excitatory. However, it may cause analgesic effect by magnetic flux density sufficient to induce at least below-sensory-threshold stimulus, more preferably at least motor-threshold stimulus.

The second envelope 24 (SE) is full-wave rectified BE 22. SE 24 includes magnetic stimulation for entire period. Therefore, in the case of symmetric BE 22 the repetition frequency of SE 24 is double repetition frequency of the original BE 22. (see FIG. 8c). The SE 24 effect may be rather inhibitory, e.g. analgesic or relaxation. Following the pain alleviating effect the muscle contraction is not painful during the increased magnetic flux density of the time-varying magnetic field. The both envelopes, FE and/or SE, may be superposed on the constant envelope (CE) inducing at least below-sensory-threshold stimulus. The superposition of CE and FE and/or SE may induce at least sensory-threshold stimulus, more preferably at least motor-threshold stimulus.

FE and/or SE may be combined in one treatment. The ratio of FE and SE may vary as well. The amplitude and/or repetition frequency of both envelopes may vary as well. The optimal value of magnetic flux density is sufficient to induce at least sensory-threshold stimulus, more preferably at least motor-threshold stimulus.

In an alternative approach of the aspect of the application in muscle stimulation the FE may be interrupted by the time period with no stimulation lasting for at least 0.1 second, more preferably at least 0.5 second, most preferably at least 1 second, the continual repeating of FE may last for at least 0.1 second, more preferably at least 0.5 second, most preferably at least 1 second as well. In another alternative approach the periodic FE and SE alternation is also applicable.

According to still another approach of the aspect of the application in muscle stimulation, the neural structure may be stimulated by alternation of FE and SE in ratio 1:1. In alternative approach FE and SE may alternate in at least 0.1 second, more preferably at least 0.5 second, most preferably at least 1 second lasting periods of each envelope. The resulting stimulation is called modulated with short periods (MSP). Therefore the MSP period is as the burst of FE and/or SE. In the preferred application the repetition of MSP is up to 20 Hz, more preferably up to 15 Hz, most preferably up to 10 Hz.

According to still another aspect of the application in muscle stimulation, the neural structure may be stimulated by envelope generated by two repetition rates interference. The first repetition rate may differ from the second repetition rate. In the exemplary embodiment the first repetition rate may be 500 Hz and the second repetition rate may be 490 Hz. The interference of the two repetition rates generates envelope of repetition frequency given by the repetition rate difference hence the interference signal repetition frequency may be 10 Hz in the exemplary application. The effect of the modulated repetition frequency in range up to 10 Hz may cause stimulation effect by the magnetic flux density induce at least sensory-threshold stimulus, more preferably motor-threshold stimulus.

According to still another application of the invention, the neural structure stimulation by time-varying magnetic field may be used for causing healing effect of a biological structure. The neural structure may be stimulated by time-varying magnetic field at repetition rate advantageously up to 175 Hz, more preferably up to 150 Hz, most preferably in the range of 50 to 130 Hz and magnetic flux density sufficient to induce at least below-sensory-threshold stimulus, more preferably at least sensory-threshold stimulus. The suitable treatment duration may be up to 120 minutes, more preferably up to 90 minutes, most preferably in the range of 30 to 60 minutes. Following the applied stimulus polarity the effect may treat inflammatory biological structures or tissue, or may improve the treatment of non-inflammatory tissue.

According to still another application of the invention, the neural structure stimulation by time-varying magnetic field may be used for improving the sleep patterns or habits. The neural structure may be stimulated by time-varying magnetic field at repetition rate in the range of 150 to 300 Hz, more preferably in the range of 175 to 250 Hz, most preferably around 200 Hz. In the preferred application the magnetic flux density is sufficient to induce at least below-sensory-threshold stimulus, more preferably at least sensory-threshold stimulus to cause sedation effect which may be used for improving the sleep patterns or habits.

According to still another application of the invention, the neural structure stimulation by time-varying magnetic field may be used for edema treatment.

According to one aspect of the application in edema treatment, the neural structure may be stimulated by repetition rate at least 80 Hz, more preferably at least 100 Hz, most preferably at least 120 Hz, by pulse duration in the range of tens to several hundreds of μs, and magnetic flux density sufficient to induce at least below-sensory-threshold stimulus, more preferably at least sensory-threshold stimulus. The suitable treatment duration may be up to 60 minutes, more preferably up to 45 minutes, most preferably in the range of 15 to 30 minutes. The application may additionally treat inflammation as well.

According to another aspect of the application in edema treatment, the neural structure may be stimulated by envelope of repetition frequency up to 75 Hz, more preferably in the range of 3 to 60 Hz, even more preferably in the range of 10 to 50 Hz, most preferably in the range of 20 to 40 Hz to cause edema reduction. The stimulation may activate the muscle pump hence the target area perfusion may be improved and the lymphatic circulation may be improved as well.

According to still another aspect of the application in edema treatment, the neural structure may be stimulated by envelope of repetition frequency up to 70 Hz, more preferably up to 60 Hz, most preferably in the range of 30 to 50 Hz. The magnetic flux density is sufficient to induce at least sensory-threshold stimulus, more preferably at least motor-threshold stimulus to cause edema reduction. The stimulation may be indicated in cases of e.g. limited movement of the biological structure. The suitable treatment duration may last up to 60 minutes, more preferably up to 45 minutes, most preferably in the range of 15 to 30 minutes.

The described applications of the invention may be used for treatment of e.g. obesity, hypertension, pain, pregnancy-related nausea or vomiting, postoperative nausea or vomiting, atopic eczema, dry mouth, enhanced blood perfusion of the uterus and placenta, hemophilia, pruritus, labor induction, Raynaud's phenomenon, sickle cell anemia pain, skin flap ischemia (during plastic surgery) or tinnitus (ringing in the ear).

All the described applications of the invention may also provide trophotropic, anti-edematous or placebo effect which contributes to improving the patient's well-being and comfort. Local metabolism may be increased as well.

All the mentioned applications may be applied in constant repetition rate and/or repetition frequency manner. The envelope modulation or combination thereof is applicable as well.

The values of magnetic flux density and repetition rate are cited in several preferred applications since the perception of the stimulation is subjective. Nevertheless, the magnetic flux density and repetition rates and/or repetition frequencies are not limited by the recited values. A person skilled in physical therapy is able to repeat and apply the therapy methods adjusting the magnetic flux density and/or repetition rate following the patient's needs. Further the applications may be used in combinations, e.g. diagnostic application and/or stimulation application.

A person skilled in the physical therapy is able to use various envelopes and waveform, e.g. pulse, sinusoidal, rectangular, square, triangular, saw-tooth, trapezoidal, exponential etc. The invention is not limited to recited envelopes.

Stimulation of neural structure by time-varying magnetic field following the recited methods may be but not limited to continuous, pulsed, randomized, or in bursts. The pulse may be but not limited to monophasic, symmetric, asymmetric, most preferably biphasic.

The methods recites above may be enabled by a device described in FIGS. 10 to 14.

Figure 10:
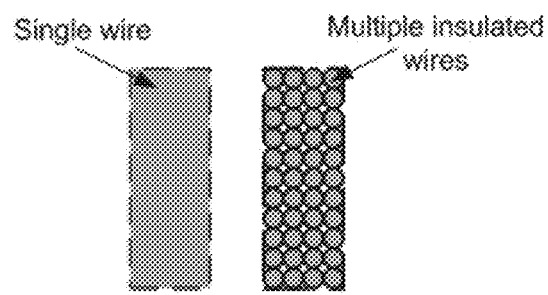
FIG. 10 is a cross section view of a coil winding.

FIG. 10 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter wires of the present coil significantly reduce self-heating of the coil and therefore increases efficiency of the present magnetic stimulation device.

$$P_{EDDY} = \frac{\pi^2 \cdot B_p^2 \cdot d^2 \cdot f^2}{6 \cdot k \cdot \rho \cdot D}, \qquad \text{Eq. 1}$$

where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; ρ is the resistivity of material (Ω·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm. The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \frac{\rho \cdot \frac{l}{S} \cdot I^2}{m} \qquad \text{Eq. 2}$$

Where: $P_R$ is the power loss heat dissipation (W); $\rho$ is the resistance ($\Omega \cdot m$); l is the length of wire (m); S is the surface area ($m^2$); I is the current (A) and m is 1 kg of wire material.

Total power loss is (Eq. 3):

$$P_{TOT} = T_{EDDY} + P_R. \qquad \text{Eq. 3}$$

Where: $P_{TOT}$ is the total power losses ($W \cdot kg^{-1}$); $P_{EDDY}$ is the power dissipation of eddy currents ($W \cdot kg^{-1}$); $P_R$ is the power loss heat dissipation ($W \cdot kg^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; build-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

Figure 11:
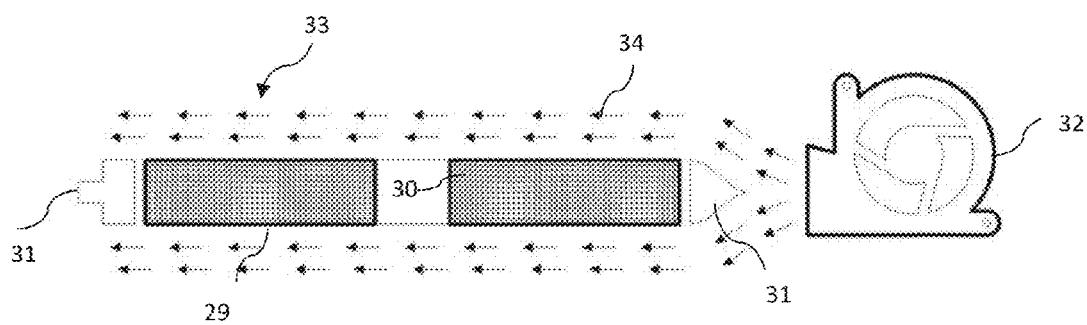
FIG. 11 is an illustrative embodiment of cross-section of the magnetic applicator.

FIG. 11 is a cross-section of the magnetic applicator which allows better flow on the lower and upper sides of the coil and thus more efficient heat dissipation. The magnetic stimulation device includes a coil 29, the circuit wires 30 and the fastening points 31 for connection of the coil to the casing of the applicator (not shown). The fastening points 31 are preferably made of flexible material however the rigid material may be used as well. The fastening points 31 may be located on the outer circumferential side of the coil. However, alternatively it is possible to put these fastening points to a lower or upper side of the coil.

The fastening points 31 connect the coil to the case of the applicator in at least one point. The fastening points 31 maintain the coil and the main part of the case of the applicator spaced apart so that fluid (which may be air or any liquid) can flow between them. At least one blower 32 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator 33 with the energy source and/or control unit of magnetic stimulation device. The connecting tube may also contain a conduit of the fluid.

The arrows 34 indicate the air flow through the applicator 33. This arrangement of the blower allows the air to bypass the coil from upper and lower (patient's) side. Outlet may be preferably placed on upper side of the casing. By placing the blower around the circumference of the coil instead of on the top/below the coil, the blower 34 does not interfere with the magnetic flux peak and therefore its lifespan and reliability is increased.

Figure 12:
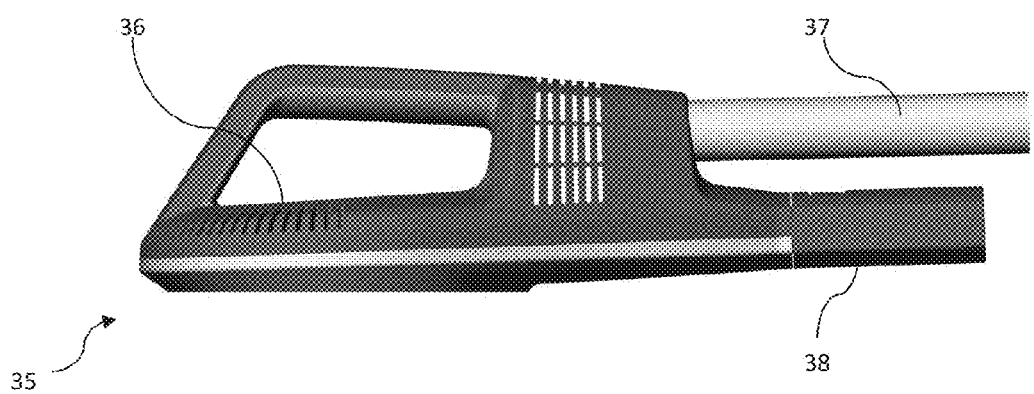
FIG. 12 is an illustrative embodiment of a casing of the magnetic applicator.

FIG. 12 is an illustrative embodiment of a casing of the magnetic applicator. The overview drawing contains casing itself 35, which might contain an outlet 36 preferably placed on upper side of the casing 35. A connecting tube 37 may not only ensure connection of the applicator with the energy source and/or control unit of magnetic stimulation device, but also connection to a source of the fluid; however the conduit of the fluid 38 may also be connected separately.

Figure 13A:
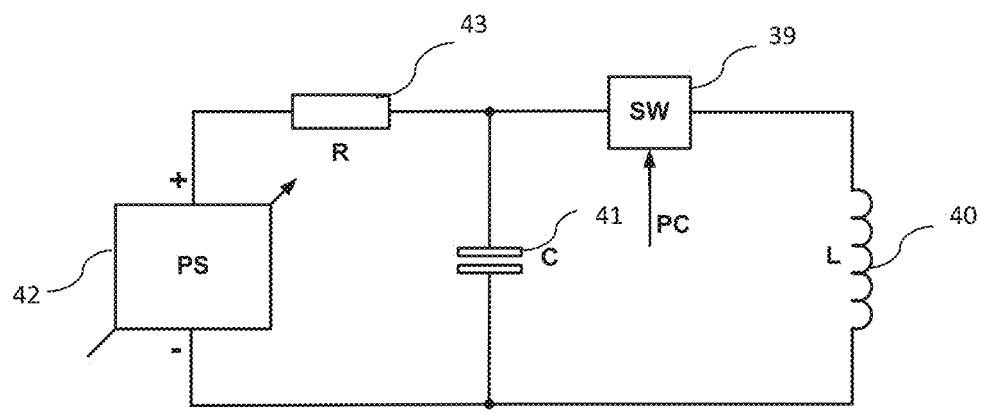
FIGS. 13A and 13B illustrates circuit for providing high power impulses to a stimulating coil
Figure 13B:
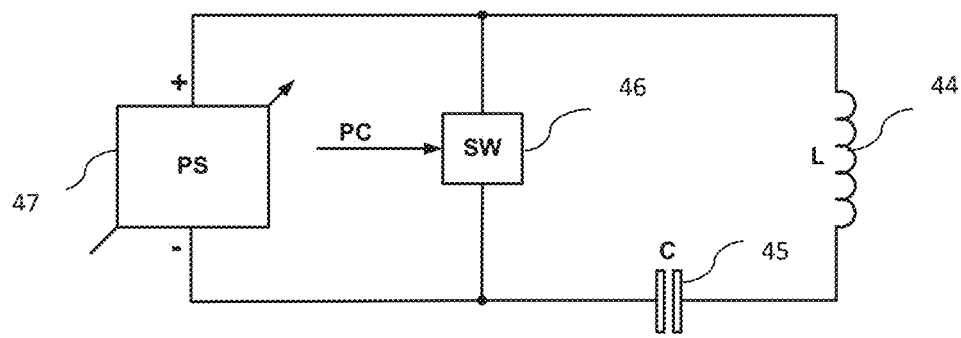

FIG. 13A and FIG. 13B illustrate circuits for providing high power pulses to the stimulating coil. FIG. 13A shows a circuit for providing high power magnetic pulses. FIG. 13B shows a circuit for providing high power pulses.

The state of art magnetic stimulation device achieves magnetic flux density of a few tenths to several ones of Tesla. To achieve this level of magnetic flux density, the energy source used generates sufficient voltage. This voltage can reach thousands of volts. In FIG. 13A the circuits for providing high power pulses to the stimulating coil contain a series connection to the switch 39 and the coil 40. The switch 39 and the coil 40 together are connected in parallel with an energy storage device 41. The energy storage device 41 is charged by the energy source 42 and the energy storage device 41 then discharges through the switching device 39 to the coil 40.

During second half-period of LC resonance, the polarity on the energy storage device 41 is reversed in comparison with the energy source 42. In this second half-period, there is a conflict between energy source 42, where voltage on positive and negative terminals is typically thousands of Volts. The energy storage device 41 is also charged to the positive and negative voltage generally to thousands of Volts. As a result, there is in the circuit, consequently, twice the voltage of the energy source 42. Hence the energy source 42 and all parts connected in the circuit are designed for a high voltage load. Therefore, the protective resistors and/or protection circuitry 43 must be placed between energy source 42 and energy storage device 41. Disadvantage of state of art solution is large amount of energy transformed to undesired heat in protective resistors and/or protection circuitry 43.

FIG. 13B shows a circuit for providing high power pulses for improved function of the magnet stimulation device. The coil 44 and an energy storage device 45 are connected in series and disposed in parallel to the switch 46. The energy storage device 45 is charged through the coil 44. To provide an energy pulse, controlled shorting of energy source 47 takes place through the switch 46. In this way the high voltage load at the terminals of the energy source 47 during the second half-period of LC resonance associated with known devices is avoided. The voltage on the terminals of energy source 47 during second half-period of LC resonance is a voltage equal to the voltage drop on the switch 46.

The switch 46 can be any kind of switch such as diode, MOSFET, JFET, IGBT, BJT, thyristor or their combination. Depending on the type of component the load of energy source 47 is reduced to a few Volts, e.g., 1-10 volts. Consequently, it is not necessary to protect the energy source 47 from a high voltage load, e.g., thousands of Volts. The use of protective resistors and/or protection circuits is reduced or eliminated. The present designs simplify the circuits used, increase efficiency of energy usage and provide higher safety.

Figure 14:
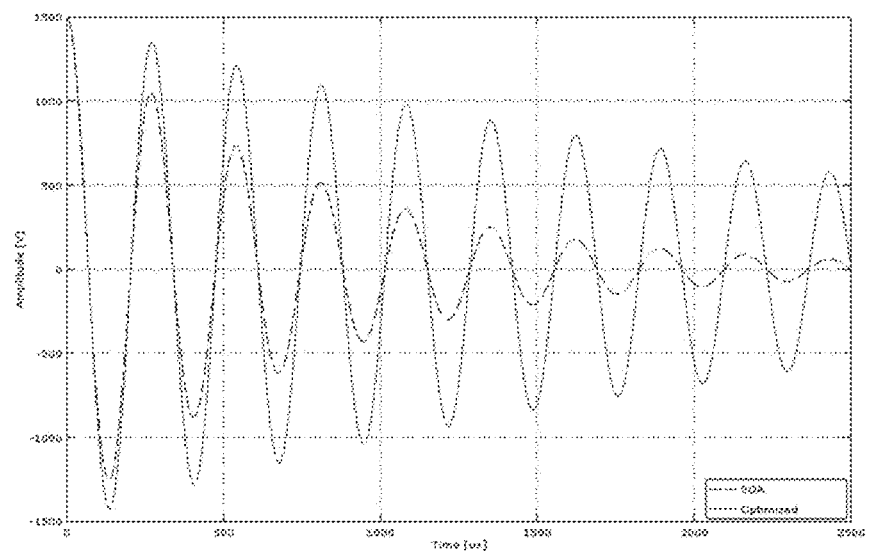
FIG. 14 is a graph showing voltage drop in the energy storage device.

FIG. 14 shows an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The device can be used for treatment/successive treatments in continual, interrupted or various duty cycle regime. The duty cycle may be higher than 10%, which means interrupted regime with the ratio up to 1 active to 9 passive time units. The ratio may possibly change during the therapy. The device enables operation defined by the peak to peak magnetic flux density on the coil surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of µs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least partial muscle contraction, action potential in cell). Based on achievement of repetition rates in order of few hundreds the device also enables assembling the magnetic pulses into the various shapes (e.g. triangular, rectangular, exponential), with the shape widths from 6 ms to several seconds or longer.

Thus, novel systems and methods have been described. Various changes and substitutions may be made of course without departing from the spirit and scope of the invention. The invention, therefore, should not be limited, except by the following claims and their equivalents.

The invention claimed is:

1. A method causing pain relief using a time-varying magnetic field applied to a peripheral neural structure of a patient, wherein the time-varying magnetic field is generated by a device including a connection to an energy source, a switching device, an energy storage device and a coil, comprising:
   a) charging the energy storage device and providing energy from the energy storage device to the coil to generate the time-varying magnetic field with a repetition rate in a range of 50 to 500 Hz;
   b) applying the time-varying magnetic field to the peripheral neural structure of the patient; and
   c) inducing an action potential within the peripheral neural structure;
   wherein a voltage drop between two successive amplitudes in the energy storage device, configured to providing energy to the coil, is less than 21%.

2. A method of stimulating a patient by a device for producing a time-varying magnetic field including a connection to an energy source, a switching device, an energy storage device and a coil, wherein the method causes pain relief and/or a myorelaxation effect via stimulation of a peripheral neural structure, comprising:
   a) providing energy from the energy storage device to the coil to generate the time-varying magnetic field;
   b) exposing the patient to the time-varying magnetic field with a repetition rate in a range of 50 to 500 Hz; and
   c) inducing an action potential within the peripheral neural structure;
   wherein a voltage drop between two successive amplitudes in the energy storage device, configured to providing energy to the coil, is less than 21%.

3. A method for treating a patient by a device which generates a time-varying magnetic field applied to a patient's body, wherein the device includes a connection to an energy source, a switching device, an energy storage device and a coil, comprising:
   a) providing energy from the energy storage device to the coil to generate the time-varying magnetic field with a magnetic flux density in a range of 0.1 to 7 T, with a repetition rate in a range of 1 to 700 Hz; and
   b) placing the coil on or adjacent to the patient's body;
   c) exposing the patient to the time-varying magnetic field; and
   d) inducing an action potential within a spinal cord and/or in a peripheral neural structure of the patient;
   wherein a voltage drop between two successive amplitudes in the energy storage device, configured to providing energy to the coil, is less than 21%.

4. A method for causing pain relief and/or a myorelaxation effect to a patient using a device which generates a time-varying magnetic field applied to a spinal cord and/or to a peripheral neural structure of the patient, wherein the device includes a connection to an energy source, a switching device, an energy storage device and a coil, comprising:

a) placing a hand-held applicator including the coil onto or adjacent to the patient or placing the patient onto a chair including the coil or placing the patient with a stand-alone applicator;
b) charging the energy storage device;
c) switching the switching device on in order to enable discharging the energy storage device to the coil;
d) generating the time-varying magnetic field by the coil with a magnetic flux density in a range of 0.1 to 7 T, with a repetition rate in a range of 1 to 700 Hz, with an impulse duration in a range of 10 to 900 μs and with a duty cycle higher than 10%;
e) applying the time-varying magnetic field in a continual and/or in pulsed regime to a spinal cord and/or to a peripheral neural structure of the patient;
f) determining a magnetic flux density of the time-varying magnetic field which causes a very first perception of an induced current by the patient;
g) increasing the magnetic flux density to reach at least an over-sensory threshold stimulus perceived by the patient; and
h) applying the time-varying magnetic field with a magnetic flux density which causes at least the over-sensory threshold stimulus perceived by the patient to a patient's body and/or limb for at least 30 seconds.

5. The method of claim 4 further comprising applying biphasic impulses of the time-varying magnetic field to the patient's body and/or limb to cause a muscle contraction.

6. The method of claim 4 further comprising assembling magnetic pulses into a sinusoidal, triangular, saw-tooth, trapezoidal, exponential, square or rectangular shape.

7. The method of claim 6 further comprising applying the time-varying magnetic field with a repetition rate in a range of 80 to 300 Hz.

8. The method of claim 4 further comprising determining the magnetic flux density of the time-varying magnetic field which causes a very first muscle contraction.

9. The method of claim 8 further comprising assembling magnetic pulses into a sinusoidal, triangular, saw-tooth, trapezoidal, exponential, square or rectangular shape.

10. The method of claim 4 wherein the coil includes a wire with a conductor diameter less than 3 mm.

11. The method of claim 10 wherein the wire is a litz-wire.

12. The method of claim 10 further comprising assembling the magnetic pulses into a sinusoidal, triangular, saw-tooth, trapezoidal, exponential, square or rectangular shape.

13. The method of claim 4 further comprising generating the time-varying magnetic field by the coil including a litz-wire; and assembling magnetic pulses into a sinusoidal, triangular, saw-tooth, trapezoidal, exponential, square or rectangular shape.

14. The method of claim 4 further comprising generating the time-varying magnetic field by the coil including a litz-wire with a conductor diameter less than 3 mm; and
applying the time-varying magnetic field with the repetition rate in a range of 80 to 300 Hz to the patient.

15. The method of claim 4 further comprising directing a cooling media in a direction parallel to the coil.

16. The method of claim 15 further comprising directing the cooling media over at least upper and lower sides of the coil.

17. The method of claim 4 wherein a blower is on a circumference of the coil.

18. The method of claim 4 wherein the coil is planar.

19. The method of claim 18 wherein a blower is on a circumference of the coil.

20. The method of claim 19 further comprising directing the cooling media over at least upper and lower sides of the coil.

21. The method of claim 4 further comprising directing air in a direction parallel to the coil.

22. The method of claim 4 wherein the coil is in serial connection with the energy storage device.

23. The method of claim 22 wherein the switching device is in parallel connection to the serial connection of the coil and the energy storage device.

24. The method of claim 22 wherein the coil includes a litz-wire.

25. The method of claim 4 further comprising placing an applicator in contact with the patient; and
applying the time-varying magnetic field with the repetition rate in a range of 100 to 300 Hz.

26. The method of claim 22 wherein the coil is planar.

27. The method of claim 4 wherein the hand-held applicator including the coil is placed onto or adjacent to the patient, or the patient is placed with the stand-alone applicator, and the coil is attached to the applicator by at least one flexible fastening point.

28. The method of claim 27 further comprising cooling the coil.

29. The method of claim 4 wherein the coil includes a litz-wire; and wherein the coil is planar.

30. The method of claim 4 wherein a voltage drop between two successive amplitudes in the energy storage device, configured to providing energy to the coil, is less than 21%.

* * * * *